(12) United States Patent
Kamon

(10) Patent No.: US 11,563,921 B2
(45) Date of Patent: Jan. 24, 2023

(54) IMAGE PROCESSING APPARATUS, ENDOSCOPE SYSTEM, AND IMAGE PROCESSING METHOD

(71) Applicant: FUJIFILM Corporation, Tokyo (JP)

(72) Inventor: Shumpei Kamon, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/079,528

(22) Filed: Oct. 26, 2020

(65) Prior Publication Data

US 2021/0044750 A1 Feb. 11, 2021

Related U.S. Application Data

(63) Continuation of application No. PCT/JP2019/016744, filed on Apr. 19, 2019.

(30) Foreign Application Priority Data

May 14, 2018 (JP) .............................. JP2018-093212

(51) Int. Cl.
*H04N 7/18* (2006.01)
*A61B 1/00* (2006.01)
(Continued)

(52) U.S. Cl.
CPC ........... *H04N 7/183* (2013.01); *A61B 1/0005* (2013.01); *A61B 1/00006* (2013.01);
(Continued)

(58) Field of Classification Search
CPC .... H04N 5/23245; H04N 5/2256; H04N 7/18; H04N 2005/2255; H04N 9/045;
(Continued)

(56) References Cited

U.S. PATENT DOCUMENTS 9,014,772 B2 * 4/2015 Yamaguchi .......... A61B 5/1459
600/309
10,765,295 B2 * 9/2020 Takahashi .......... H04N 9/04557
(Continued)

FOREIGN PATENT DOCUMENTS

JP 2011160848 8/2011
JP 2012157559 8/2012
(Continued)

OTHER PUBLICATIONS

"Search Report of Europe Counterpart Application", dated Jun. 9, 2021, pp. 1-5.
"International Search Report (Form PCT/ISA/210) of PCT/JP2019/016744," dated Jul. 9, 2019, with English translation thereof, pp. 1-4.
"Written Opinion of the International Searching Authority (Form PCT/ISA/237) of PCT/JP2019/016744," dated Jul. 9, 2019, with English translation thereof, pp. 1-7.

*Primary Examiner* — Richard A Hansell, Jr.
(74) *Attorney, Agent, or Firm* — JCIPRNET

(57) ABSTRACT

An image processing apparatus according to a first aspect of the present invention acquires a first image and a second image in a first image acquisition mode, or a second image acquisition mode in which a second image acquisition ratio is higher than in the first image acquisition mode, on the basis of a detection result of a specific target (whether or not a specific target has been detected, what type of specific target). For example, in accordance with whether or not a specific target has been detected and the type of specific target, the first image and the second image can be acquired in the first image acquisition mode in a case where the necessity for acquiring the second image is low, whereas the first image and the second image can be acquired in the second image acquisition mode, in which the second image (Continued)

acquisition ratio is high, in a case where the necessity for acquiring the second image is high.

17 Claims, 18 Drawing Sheets

(51) Int. Cl.
*A61B 1/045* (2006.01)
*A61B 1/06* (2006.01)
*G06K 9/62* (2022.01)
*H04N 5/225* (2006.01)
*H04N 5/232* (2006.01)
*G06V 10/25* (2022.01)
*A61B 1/04* (2006.01)

(52) U.S. Cl.
CPC ........ *A61B 1/000094* (2022.02); *A61B 1/044* (2022.02); *A61B 1/045* (2013.01); *A61B 1/063* (2013.01); *A61B 1/0638* (2013.01); *A61B 1/0646* (2013.01); *G06K 9/6267* (2013.01); *G06V 10/25* (2022.01); *H04N 5/2256* (2013.01); *H04N 5/23245* (2013.01); *H04N 7/18* (2013.01); *H04N 2005/2255* (2013.01)

(58) Field of Classification Search
CPC ............. H04N 5/2354; H04N 5/23218; H04N 5/23293; A61B 1/00006; A61B 1/0005; A61B 1/005; A61B 1/045; A61B 1/063; A61B 1/0638; A61B 1/0646; A61B 1/00009; G06K 9/3233; G06K 9/6267; G06K 9/6202; G06K 9/2018; G06K 2209/05; G06K 9/6271
See application file for complete search history.

(56) References Cited

U.S. PATENT DOCUMENTS

| | | | |
|---|---|---|---|
| 10,776,915 B2 * | 9/2020 | Shigeta | A61B 1/0005 |
| 10,867,367 B2 * | 12/2020 | Sasaki | G06T 3/4007 |
| 2012/0078046 A1 * | 3/2012 | Sasaki | A61B 1/000094 600/109 |
| 2012/0157775 A1 * | 6/2012 | Yamaguchi | A61B 1/0638 600/180 |
| 2012/0197080 A1 | 8/2012 | Murayama | |
| 2012/0274754 A1 | 11/2012 | Tsuruoka | |
| 2015/0238126 A1 * | 8/2015 | Saito | A61B 1/000094 600/339 |
| 2017/0112356 A1 * | 4/2017 | Mitsui | H04N 7/183 |
| 2018/0114319 A1 * | 4/2018 | Kono | A61B 1/126 |
| 2018/0250094 A1 * | 9/2018 | Sugie | A61B 1/0005 |
| 2021/0145266 A1 * | 5/2021 | On | G06T 7/174 |

FOREIGN PATENT DOCUMENTS

| | | | |
|---|---|---|---|
| JP | 2012213550 | 11/2012 | |
| JP | 2016062488 | 4/2016 | |
| JP | 2017064091 | 4/2017 | |
| WO | WO-2020035929 A1 * | 2/2020 | ......... A61B 1/00009 |

* cited by examiner

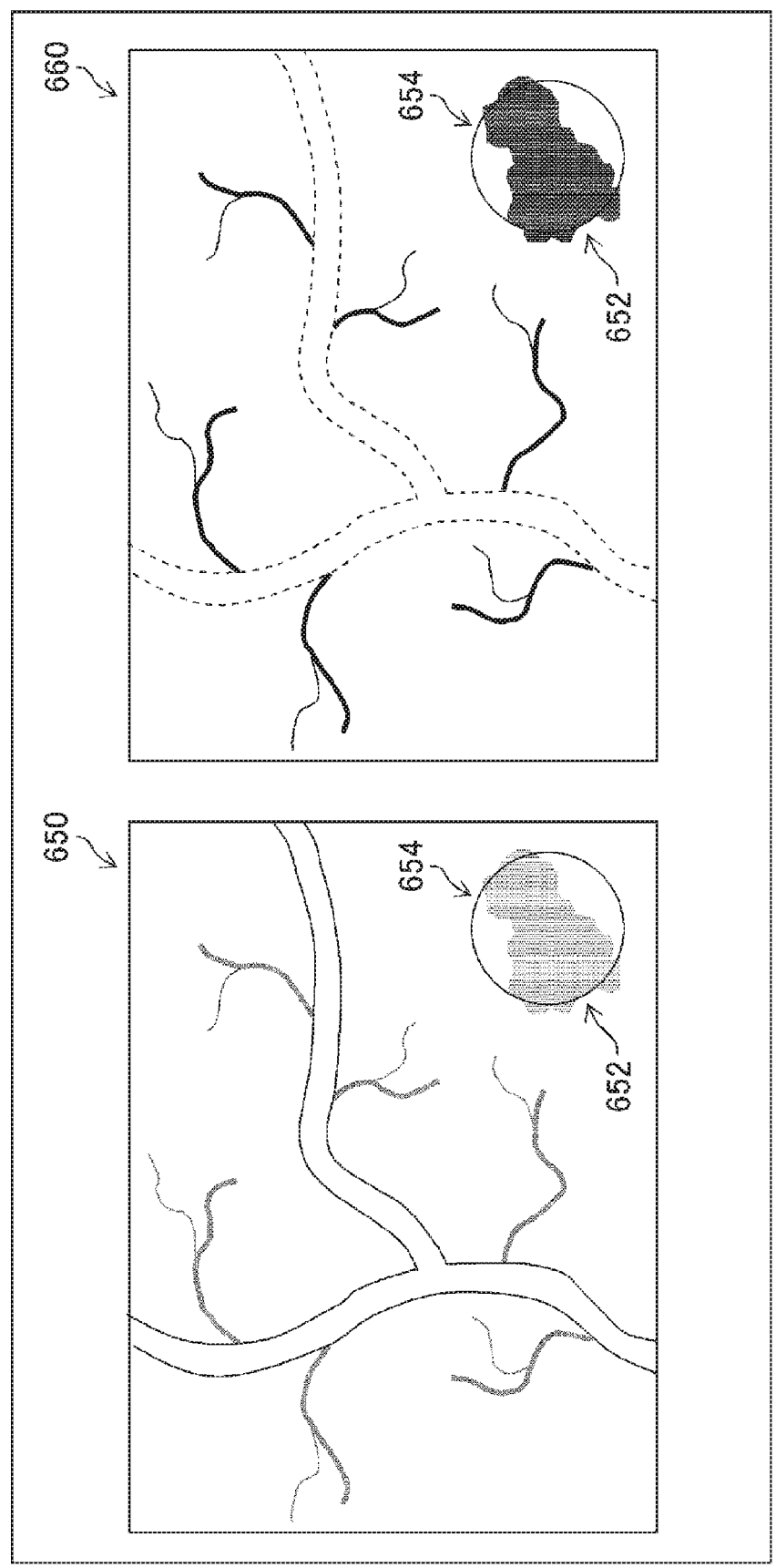

IMAGE PROCESSING APPARATUS, ENDOSCOPE SYSTEM, AND IMAGE PROCESSING METHOD

CROSS-REFERENCE TO RELATED APPLICATIONS

This application is a Continuation of PCT International Application No. PCT/JP2019/016744 filed on Apr. 19, 2019, which claims priority under 35 U.S.C § 119(a) to Japanese Patent Application No. 2018-093212 filed on May 14, 2018. Each of the above application(s) is hereby expressly incorporated by reference, in its entirety, into the present application.

BACKGROUND OF THE INVENTION

1. Field of the Invention

The present invention relates to an image processing apparatus, an endoscope system, and an image processing method, and specifically relates to an image processing apparatus, an endoscope system, and an image processing method that acquire images by using a plurality of types of observation light.

2. Description of the Related Art

In medical practice, an image of a subject captured by using medical equipment is used in diagnosis, treatment, or the like. "What structure of a photographic subject is clearly (or unclearly) seen in a captured image" depends on the observation light used for imaging. For example, an image captured under special light, such as narrow-band light with a strong short-wavelength component, depicts blood vessels in a surface layer with a favorable contrast and is thus suitable for detecting a lesion. On the other hand, an image captured under special light with a strong long-wavelength component depicts blood vessels in a deep layer with a favorable contrast. Meanwhile, observation by a medical doctor is often performed by using normal light (white light), not special light. In this way, in imaging it is preferable to radiate observation light suitable for the usage purpose of an image or a target.

For example, JP2016-062488A is known as a technique for detecting a specific target from an image acquired by using observation light. JP2016-062488A describes detecting of an agent and/or equipment used in a test by image recognition. In addition, for example, JP2012-213550A is known as a technique for switching observation light in accordance with an observation target. JP2012-213550A describes switching of a wavelength set of narrow-band observation light in accordance with the depth of a layer to be observed. The wavelength of observation light is short in the wavelength set for surface-layer observation, whereas the wavelength of observation light is long in the wavelength set for deep-layer observation.

An endoscope is used for various purposes, such as observation and treatment, and various targets may be detected from an image acquired thereby. For example, a region of interest, such as a lesion, may be detected in the case of observation, whereas a tool such as a treatment tool, equipment, or an agent may be detected in the case of treatment. In this case, appropriate observation light varies according to a target to be detected.

As imaging using observation light suitable for a target, "multi-frame imaging" may be performed in which images corresponding to a plurality of different types of observation light are acquired while sequentially switching among the plurality of types of observation light at a determined frame rate. For example, it is possible to acquire an image by using special light at a determined rate while continuing observation with an image acquired by mainly using normal light, thereby accurately detecting a region of interest. Such multi-frame imaging makes it possible to detect a region of interest with higher accuracy while presenting a normal-light image familiar to a user.

SUMMARY OF THE INVENTION

An object of the present invention is to provide an image processing apparatus, an endoscope system, and an image processing method that are capable of acquiring an image in an appropriate imaging mode on the basis of a detection result of a specific target.

To achieve the above-described object, an image processing apparatus according to a first aspect of the present invention includes: an image acquiring unit that acquires a first image and a second image that are captured at different times, the image acquiring unit acquiring the first image that is captured by using first observation light and the second image that is captured by using second observation light different from the first observation light; a mode control unit that causes the image acquiring unit to acquire the first image and the second image in either a first image acquisition mode of acquiring the first image and the second image such that a ratio of the number of acquired frames of the second image to the number of acquired frames of the first image in a predetermined time range is a first ratio, or a second image acquisition mode of acquiring the first image and the second image such that a ratio of the number of acquired frames of the second image to the number of acquired frames of the first image in the time range is a second ratio higher than the first ratio; a specific target detecting unit that detects a specific target from the first image and/or the second image; and a display control unit that causes a display apparatus to display the first image. The mode control unit causes the image acquiring unit to acquire the first image and the second image in the first image acquisition mode or the second image acquisition mode on the basis of a detection result of the specific target.

In the case of the above-described multi-frame imaging, the frame rate of an image for observation (for example, a normal-light image) decreases in accordance with the frames at which an image for detecting a region of interest (for example, a special-light image) is acquired, and thus it is not always preferable to perform multi-frame imaging over an entire time period of a test. In view of this circumstance, it is preferable to set an imaging mode (whether or not to perform multi-frame imaging, and a condition such as observation light and/or the rate in the case of performing multi-frame imaging) in consideration of "whether or not a target has been detected from an image, what type of target in a case where a target has been detected". However, in the above-mentioned JP2012-213550A, although imaging is performed by switching between a plurality of types of observation light in accordance with a target (the depth of a layer to be observed), a consideration is not made about how to set an imaging mode in accordance with a target detected from an image.

In contrast to this related art, in the first aspect, the first image and the second image are acquired in the first image acquisition mode, or the second image acquisition mode in which a second image acquisition ratio is higher than in the first image acquisition mode, on the basis of a detection result of a specific target (whether or not a specific target has been detected, what type of specific target). For example, in accordance with whether or not a specific target has been detected and the type of specific target, the first image and the second image can be acquired in the first image acquisition mode in a case where the necessity for acquiring the second image is low, whereas the first image and the second image can be acquired in the second image acquisition mode, in which the second image acquisition ratio is higher than in the first image acquisition mode, in a case where the necessity for acquiring the second image is high. In this way, according to the first aspect, images (the first image and the second image) can be acquired in an appropriate imaging mode based on a detection result of a specific target. The first image is displayed on the display apparatus in any image acquisition mode, and thus observation with the first image can be continued regardless of the image acquisition mode.

In the first aspect and the following individual aspects, the "specific target" is a target that is important in terms of a usage purpose of an image, and may be determined in accordance with a usage purpose of an image. For example, an example of a specific target in the case of observation may be a region of interest, such as a lesion (also referred to as a region of concern), and an example of a specific target in the case of treatment may be a tool, such as a treatment tool, equipment, or an agent, but the specific target is not limited to these examples. The values of the first ratio and the second ratio (corresponding to a first image acquisition ratio and a second image acquisition ratio) may be set in accordance with the purpose of a test, the type of specific target, or the like. The values may be set in accordance with designation by a user, or may be set by the image processing apparatus without designation by a user.

In the first aspect and the following individual aspects, one of the first observation light and the second observation light may be white light and the other may be narrow-band light, or both may be narrow-band light of different types. Each of the first observation light and the second observation light may be light emitted by a light source, or may be light generated by applying, to light emitted by a light source (for example, white light), a filter that allows a specific wavelength range to pass therethrough. In the case of using narrow-band light as the first observation light and/or the second observation light, the narrow-band light to be used may be narrow-band light radiated by a light source for narrow-band light, or may be narrow-band light generated by applying, to white light, a filter that allows a specific wavelength range to pass therethrough. In this case, the filter may be sequentially switched to radiate different types of narrow-band light at different timings.

In the first aspect, the first image captured by using the first observation light and the second image captured by using the second observation light are acquired. Because the second observation light is not used to capture the first image and the first observation light is not used to capture the second image, degradation of the image quality of the first image and the second image caused by insufficient wavelength separation does not occur.

In the first aspect and the following individual aspects, "the first observation light is different from the second observation light" means that at least one of the wavelength range or the spectrum is not identical between the first observation light and the second observation light. In addition, the second image can be displayed when necessary (for example, in accordance with input of a user's instruction or in accordance with a result of processing the second image).

The first image and the second image may be medical images obtained by capturing a subject, such as a living body.

As a light source used to capture a medical image, a light source that generates light in a white range, light including a plurality of wavelengths (narrow-band light) as the white range, infrared light, or excitation light can be used. The medical image acquired in the first aspect may be a normal-light image acquired by radiating light in the white range or light in a plurality of wavelength ranges as the light in the white range, or may be a special-light image acquired on the basis of a normal-light image and having information of a specific wavelength range.

In an image processing apparatus according to a second aspect, in the first aspect, the specific target detecting unit is a region-of-interest detecting unit that detects a region of interest, in a case where the region-of-interest detecting unit has not detected the region of interest, the mode control unit causes the image acquiring unit to acquire the first image and the second image in the first image acquisition mode, and in a case where the region-of-interest detecting unit has detected the region of interest, the mode control unit causes the image acquiring unit to acquire the first image and the second image in the second image acquisition mode until a first termination condition is satisfied. In the second aspect, in a case where a region of interest has not been detected, the first image acquisition mode is used because it is preferable not to decrease the frame rate of displaying an image (displaying the first image) as much as possible, and in a case where a region of interest has been detected, the second image acquisition mode, in which the second image acquisition ratio is higher than in the first image acquisition mode, is used. The second image can be used to, for example, measure or classify a region of interest. The region of interest is also referred to as a region of concern.

In the second aspect, the region-of-interest detecting unit may perform region-of-interest detection processing on the first image and/or the second image. The detection processing may be performed on all the frames of the first image and/or the second image or may be intermittently performed on some frames. In the second aspect, for example, the elapse of a set time, acquisition of a designated number of still images, no more detection of a region of interest, a termination instruction from a user, or the like can be used as the "first termination condition", but the first termination condition is not limited to these examples.

In an image processing apparatus according to a third aspect, in the second aspect, in a case where the first termination condition is satisfied, the mode control unit causes the image acquiring unit to acquire the first image and the second image in the first image acquisition mode. According to the third aspect, in a case where the first termination condition is satisfied, a decrease in the frame rate of displaying an image (displaying the first image) can be prevented by using the first image acquisition mode.

In an image processing apparatus according to a fourth aspect, in the second or third aspect, the image processing apparatus further includes a classifying unit that performs classification of the region of interest on the basis of at least the second image of the first image and the second image. In the fourth aspect, in the case of imaging the inside of a living body, it is possible to perform, as "classification", determination of the type of polyp (neoplastic or non-neoplastic), diagnosis of the stage of cancer, or the position in a lumen (an imaging position).

In an image processing apparatus according to a fifth aspect, in the fourth aspect, the display control unit causes the display apparatus to display information indicating a result of the classification. In the fifth aspect, the information can be displayed by using, for example, characters, numerals, figures, symbols, colors, or the like corresponding to the classification result, and accordingly a user is able to easily recognize the information about a region of interest. The information may be displayed by being superimposed on an image, or may be displayed separately from the image.

In an image processing apparatus according to a sixth aspect, in the first aspect, the specific target detecting unit is a detector that detects an agent and/or equipment used for a subject, and in a case where the detector has detected the agent and/or the equipment, the mode control unit causes the image acquiring unit to acquire the first image and the second image in the first image acquisition mode until a second termination condition is satisfied. During treatment, a precise operation is often required and thus a decrease in the frame rate of displaying an image (displaying the first image) is not preferable. In addition, it is considered that, in the stage of performing treatment, a discrimination result of a lesion has been confirmed and thus automatic discrimination using a second image is not necessary. Thus, it is preferable to use the first image acquisition mode, in which the first image acquisition ratio is higher than in the second image acquisition mode, in a case where an agent and/or equipment used for treatment or the like has been detected.

In a case where a colorant or a dye is applied to a lesion, a decrease in the frame rate of displaying an image (displaying the first image) is not preferable because the user is to carefully examine a minute structure of the lesion. Thus, it is preferable to use the first image acquisition mode, in which the first image acquisition ratio is higher than in the second image acquisition mode, in a case where an agent such as a pigment or a dye has been detected. In view of this circumstance, in the sixth aspect, in a case where the detector has detected an agent and/or equipment, the mode control unit causes the image acquiring unit to acquire the first image and the second image in the first image acquisition mode until the second termination condition is satisfied, and thus the user is able to accurately perform treatment or observation of a lesion. The second termination condition may be, for example, the elapse of a predetermined time, no more detection of an agent and/or equipment, acquisition of a predetermined number of still images, a termination instruction from the user, or the like, but is not limited to these examples.

As described above regarding the first aspect, the second image acquisition ratio is higher in the second image acquisition mode than in the first image acquisition mode, and thus the first image acquisition ratio is higher in the first image acquisition mode than in the second image acquisition mode.

In an image processing apparatus according to a seventh aspect, in any one of the first to sixth aspects, the mode control unit has a ratio setting unit that sets the first ratio and/or the second ratio. The first ratio and/or the second ratio may be set in accordance with designation by a user, or may be set by the ratio setting unit without designation by a user.

In an image processing apparatus according to an eighth aspect, in the seventh aspect, the ratio setting unit sets the first ratio to zero and sets the second ratio to a value greater than zero. In the eighth aspect, the first ratio is set to zero, and thus in the first image acquisition mode multi-frame imaging is OFF and only the first image is acquired. On the other hand, the second ratio is set to a value greater than zero, and thus in the second image acquisition mode the first image and the second image are acquired in multi-frame imaging.

In an image processing apparatus according to a ninth aspect, in any one of the first to eighth aspects, the image processing apparatus further includes: a parameter calculating unit that calculates a parameter for aligning the first image and the second image; and an image generating unit that generates an alignment first image by applying the parameter to the first image. The display control unit causes the display apparatus to display the alignment first image at a timing when the second image is acquired. In the ninth aspect, a parameter for alignment is applied to the first image to generate an alignment first image. Thus, a substantial decrease in the frame rate of the first image can be prevented, and a change in the tint and structure of a photographic subject can be reduced between frames (between a frame of the first image and a frame of the alignment first image). In the ninth aspect and the following individual aspects, the "alignment first image" means "a first image at an imaging time of a second image, generated by applying an alignment parameter to a first image".

In the ninth aspect, the parameter calculating unit may calculate, as a parameter, a parameter about at least one of relative movement, rotation, or deformation between the first image and the second image. "Deformation" may include enlargement or reduction. In addition, the parameter calculating unit may calculate, as a parameter, a parameter for performing projective transformation between the first image and the second image, and the image generating unit may generate an alignment first image by performing projective transformation based on the calculated parameter on the first image.

In an image processing apparatus according to a tenth aspect, in the ninth aspect, the parameter calculating unit calculates the parameter for aligning the second image and the first image, the first image being captured at an imaging time that is before an imaging time of the second image and that has a temporal difference smaller than or equal to a threshold value from the imaging time of the second image. In the case of using the first image captured at an imaging time after the imaging time of the second image, generation and display of an alignment first image may be delayed depending on a temporal difference between the imaging times. In a case where the temporal difference between the imaging times exceeds the threshold value, an imaging range, an imaging angle, or the like may be changed as a result of a motion of a photographic subject or the like, and the alignment accuracy may decrease. In view of this circumstance, in the tenth aspect, the first image captured at an imaging time that is before an imaging time of the second image and that has a temporal difference smaller than or equal to the threshold value from the imaging time of the second image is acquired, and thus it is possible to generate an alignment first image having a small change in the structure of a photographic subject compared to the first image.

In an image processing apparatus according to an eleventh aspect, in any one of the first to tenth aspects, the image acquiring unit acquires, as the second image, an image captured by using the second observation light, the second observation light being light whose center wavelength is shorter than a center wavelength of the first observation light. The structure of a photographic subject seen in an image varies according to the wavelength of observation light, and thus it is preferable to use observation light having a short wavelength to capture and detect a minute structure of a lesion or the like. In the eleventh aspect, detection or the like of a minute structure can be accurately performed by using the second image while observation is continued by displaying the first image.

To achieve the above-described object, an endoscope system according to a twelfth aspect of the present invention includes: the image processing apparatus according to any one of the first to eleventh aspects; the display apparatus; an endoscope that has an insertion section and a handheld operation section, the insertion section being to be inserted into a subject and having a tip rigid part, a bending part connected to a base end side of the tip rigid part, and a soft part connected to a base end side of the bending part, the handheld operation section being connected to a base end side of the insertion section; a light source apparatus that irradiates the subject with the first observation light or the second observation light; and an imaging unit that has an imaging lens which forms an optical image of the subject and an imaging device on which the optical image is formed by the imaging lens. The imaging lens is provided at the tip rigid part. The endoscope system according to the twelfth aspect includes the image processing apparatus according to any one of the first to eleventh aspects, and is thus capable of acquiring an image in an appropriate imaging mode (the first image acquisition mode or the second image acquisition mode) based on a detection result of a specific target. In addition, the first image is displayed on the display apparatus in any image acquisition mode, and thus observation with the first image can be continued regardless of the image acquisition mode.

The endoscope system according to the twelfth aspect includes the image processing apparatus according to any one of the first to eleventh aspects, and thus an advantageous effect of including the image processing apparatus (the first image acquisition mode or the second image acquisition mode can be appropriately set on the basis of a detection result of a specific target) is acquired. That is, it is possible to prevent that the second image acquisition mode is set and the second image acquisition ratio increases even in a case where the necessity for the second image is low and increased repetition of radiation and non-radiation of observation light unnecessarily hastens degradation of the light source.

In the twelfth aspect, light emitted by the light source may be used as observation light, or light generated by applying, to light emitted by the light source, a filter that allows a specific wavelength range to pass therethrough may be used as observation light. For example, in the case of using narrow-band light as the first observation light and/or the second observation light, light radiated by a narrow-band light source may be used as observation light, or light generated by applying, to white light, a filter that allows a specific wavelength range to pass therethrough may be used as observation light. In this case, the filter applied to white light may be sequentially switched to radiate different types of narrow-band light at different timings.

In an endoscope system according to a thirteenth aspect, in the twelfth aspect, the light source apparatus irradiates the subject with the first observation light, the first observation light being white light including light in a red wavelength range, a blue wavelength range, and a green wavelength range, and irradiates the subject with the second observation light, the second observation light being narrow-band light corresponding to any one of the red wavelength range, the blue wavelength range, and the green wavelength range. According to the thirteenth aspect, it is possible to perform detection and classification of a region of interest by using the second image captured by using narrow-band light (second observation light) while performing observation by displaying the first image captured by using white light (first observation light). Alternatively, narrow-band light corresponding to a purple wavelength range and an infrared wavelength range may be used.

In an endoscope system according to a fourteenth aspect, in the thirteenth aspect, the light source apparatus includes a white-light laser light source that radiates white-light laser as excitation light; a fluorescent body that emits the white light as the first observation light when irradiated with the white-light laser; and a narrow-band-light laser light source that radiates the narrow-band light as the second observation light. In the case of using a laser light source for excitation light to acquire white light as the first observation light, a high second image acquisition ratio increases repetition of radiation and non-radiation of the first observation light. Accordingly, repetition of excitation and non-excitation of the white-light laser light source increases and degradation of the light source may be hastened. However, the endoscope system according to the fourteenth aspect includes the image processing apparatus according to any one of the first to eleventh aspects, and thus an advantageous effect of including the image processing apparatus (the first image acquisition mode or the second image acquisition mode can be appropriately set on the basis of a detection result of a specific target) is acquired. That is, it is possible to prevent that the second image acquisition mode is set and the second image acquisition ratio increases even in a case where the necessity for the second image is low (for example, in a case where a specific target is not detected) and increased repetition of radiation and non-radiation of the first observation light unnecessarily hastens degradation of the light source.

In an endoscope system according to a fifteenth aspect, in the thirteenth aspect, the light source apparatus includes a white light source that emits the white light; a white-light filter that allows the white light to pass therethrough; a narrow-band-light filter that allows a component of the narrow-band light in the white light to pass therethrough; and a first filter switching control unit that inserts the white-light filter or the narrow-band-light filter to an optical path of the white light emitted by the white light source. In the case of generating a plurality of types of observation light (white light and narrow-band light) by switching a filter, lack of synchronization between the switching of the filter and the read-out timing of an image sensor (an imaging device) may cause an imbalance in the color of the first image and/or the second image. However, since the endoscope system according to the fifteenth aspect includes the image processing apparatus according to any one of the first to eleventh aspects, an advantageous effect of including the image processing apparatus (the first image acquisition mode or the second image acquisition mode can be set on the basis of a detection result of a specific target) is acquired. That is, it is possible to reduce the possibility that the second image acquisition mode is set and the number of times of switching of the light source or the filter increases even in a case where the necessity for the second image is low (for example, a case were a specific target is not detected), and the color balance of the first image and/or the second image is lost.

In an endoscope system according to a sixteenth aspect, in the twelfth aspect, the light source apparatus irradiates the subject with the first observation light, the first observation light being first narrow-band light that corresponds to any one of a red wavelength range, a blue wavelength range, and a green wavelength range, and irradiates the subject with the second observation light, the second observation light being second narrow-band light that corresponds to any one of the red wavelength range, the blue wavelength range, and the green wavelength range and that has a wavelength range different from a wavelength range of the first narrow-band light. The sixteenth aspect defines an aspect of using a plurality of types of narrow-band light. For example, a combination of a plurality of types of blue narrow-band light having different wavelengths, a combination of blue narrow-band light and green narrow-band light, a combination of a plurality of types of red narrow-band light having different wavelengths, or the like may be used, but the observation light is not limited to these combinations. Narrow-band light corresponding to a purple wavelength range and an infrared wavelength range may be used.

In an endoscope system according to a seventeenth aspect, in the sixteenth aspect, the light source apparatus includes a white light source that emits white light including light in the red wavelength range, the blue wavelength range, and the green wavelength range; a first-narrow-band-light filter that allows a component of the first narrow-band light in the white light to pass therethrough; a second-narrow-band-light filter that allows a component of the second narrow-band light in the white light to pass therethrough; and a second filter switching control unit that inserts the first-narrow-band-light filter or the second-narrow-band-light filter to an optical path of the white light emitted by the white light source. In the case of generating a plurality of types of observation light (first narrow-band light and second narrow-band light) by switching a filter by the second filter switching control unit, lack of synchronization between the switching of the filter and the read-out timing of an image sensor (an imaging device) may cause an imbalance in the color of the first image and/or the second image. However, since the endoscope system according to the seventeenth aspect includes the image processing apparatus according to any one of the first to eleventh aspects, an advantageous effect of including the image processing apparatus (the first image acquisition mode or the second image acquisition mode can be set on the basis of a detection result of a specific target) is acquired. That is, it is possible to reduce the possibility that the second image acquisition mode is set and the number of times of switching of the light source or the filter increases even in a case where the necessity for the second image is low (for example, a case were a specific target is not detected), and the color balance of the first image and/or the second image is lost.

To achieve the above-described object, an image processing method according to an eighteenth aspect of the present invention includes: an image acquisition step of acquiring a first image and a second image that are captured at different times, the image acquisition step acquiring the first image that is captured by using first observation light and the second image that is captured by using second observation light different from the first observation light; a mode control step of causing the first image and the second image to be acquired in the image acquisition step in either a first image acquisition mode of acquiring the first image and the second image such that a ratio of the number of acquired frames of the second image to the number of acquired frames of the first image in a predetermined time range is a first ratio, or a second image acquisition mode of acquiring the first image and the second image such that a ratio of the number of acquired frames of the second image to the number of acquired frames of the first image in the time range is a second ratio higher than the first ratio; and a specific target detection step of detecting a specific target from the first image and/or the second image. The mode control step causes the first image and the second image to be acquired in the image acquisition step in the first image acquisition mode or the second image acquisition mode on the basis of a detection result of the specific target. According to the eighteenth aspect, as in the first aspect, images (the first image and the second image) can be acquired in an appropriate imaging mode on the basis of a detection result of a specific target.

The image processing method according to the eighteenth aspect may further include configurations similar to those according to the second to eleventh aspects. In addition, a program that causes the endoscope system to execute the image processing methods according to these aspects, and a non-transitory recording medium storing a computer-readable code of the program may be included in an aspect of the present invention.

As described above, the image processing apparatus, the endoscope system, and the image processing method according to the present invention are capable of acquiring an image in an appropriate imaging mode on the basis of a detection result of a specific target.

BRIEF DESCRIPTION OF THE DRAWINGS

FIG. 15 is a diagram illustrating a display example of a first image and a second image;

DESCRIPTION OF THE PREFERRED EMBODIMENTS

Hereinafter, an embodiment of an image processing apparatus, an endoscope system, and an image processing method according to the present invention will be described in detail with reference to the attached drawings.

First Embodiment

Figure 1:
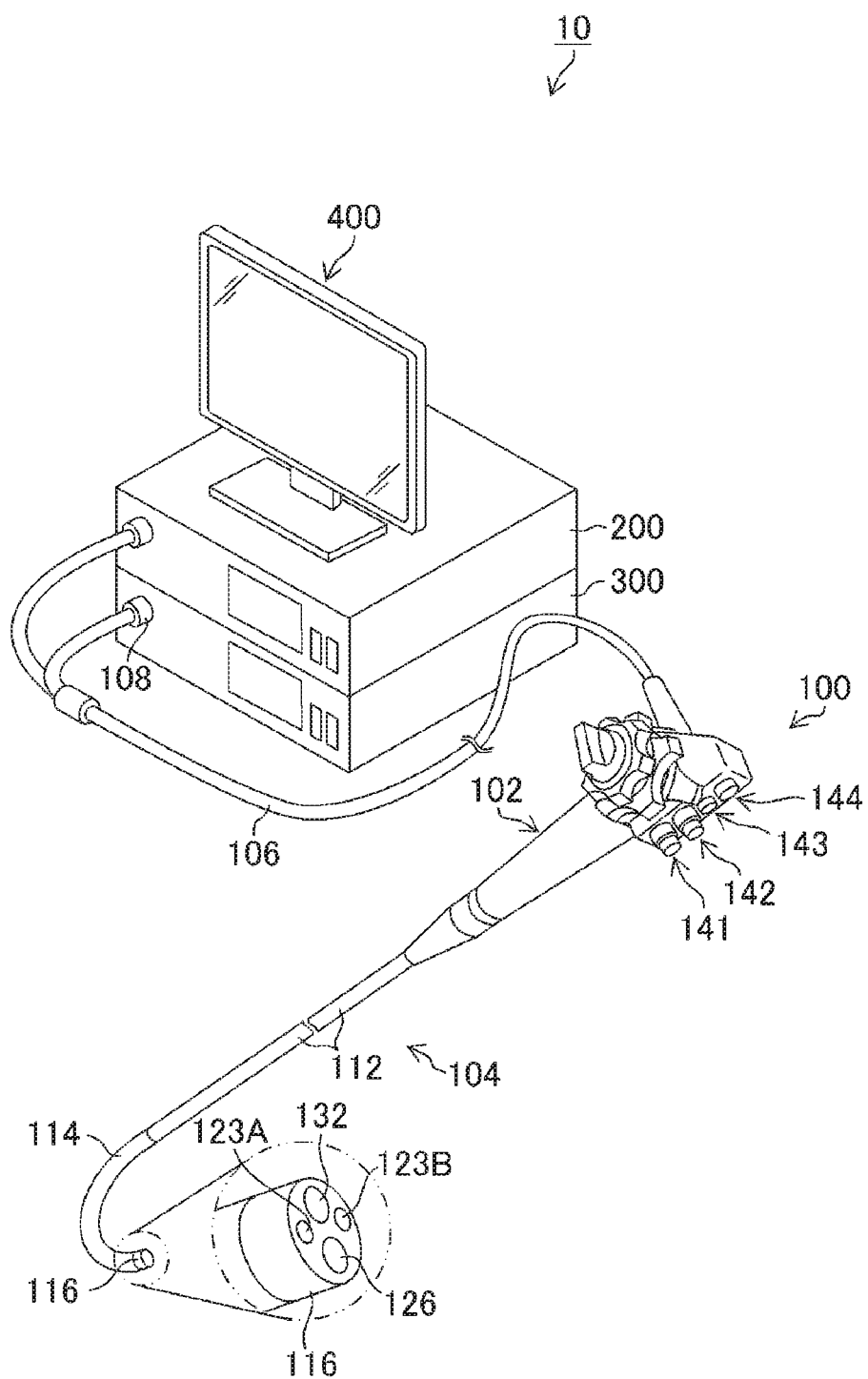
FIG. 1 is an external appearance diagram of an endoscope system according to a first embodiment.
Figure 2:
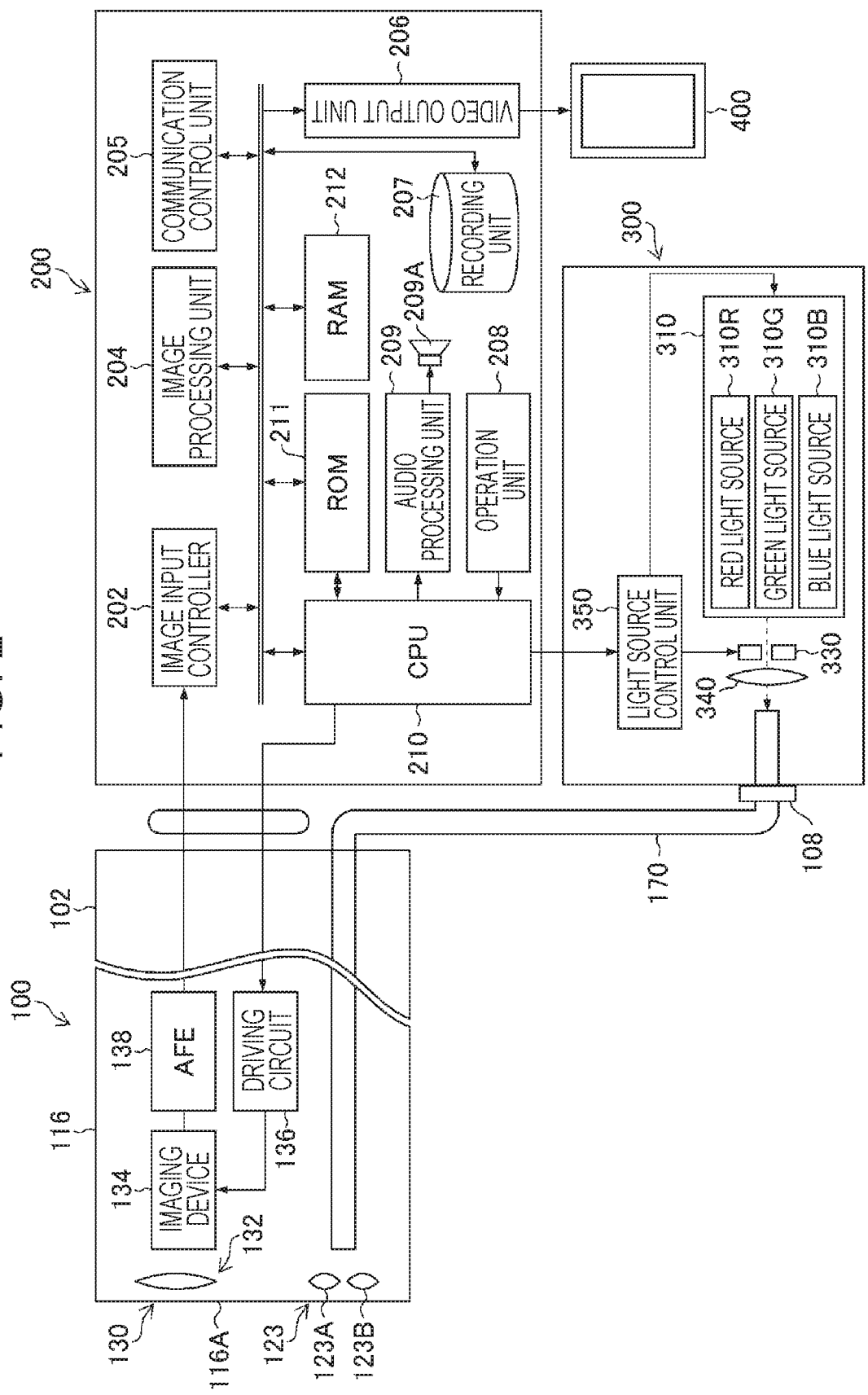
FIG. 2 is a block diagram illustrating the configuration of the endoscope system.

FIG. 1 is an external appearance diagram illustrating an endoscope system 10 (an image processing apparatus, a diagnosis assistance apparatus, an endoscope system, a medical image processing apparatus) according to a first embodiment, and FIG. 2 is a block diagram illustrating the configuration of a main part of the endoscope system 10. As illustrated in FIGS. 1 and 2, the endoscope system 10 is constituted by an endoscope main body 100 (an endoscope), a processor 200 (a processor, an image processing apparatus, a medical image processing apparatus), a light source apparatus 300 (a light source apparatus), and a monitor 400 (a display apparatus).

Configuration of Endoscope Main Body

The endoscope main body 100 includes a handheld operation section 102 (an operation section) and an insertion section 104 (an insertion section) that communicates with the handheld operation section 102. An operator (a user) operates the handheld operation section 102 while grasping it and inserts the insertion section 104 into a body of a subject (a living body) to perform observation. The handheld operation section 102 is provided with an air/water supply button 141, a suction button 142, a function button 143 to which various functions are allocated, and an imaging button 144 for receiving an imaging instruction operation. The insertion section 104 is constituted by a soft part 112 (i.e., a flexible tube part), a bending part 114 (a bending part), and a tip rigid part 116 (a tip rigid part), which are arranged in this order from the handheld operation section 102 side. That is, the bending part 114 is connected to a base end side of the tip rigid part 116, and the soft part 112 is connected to a base end side of the bending part 114. The handheld operation section 102 is connected to a base end side of the insertion section 104. The user is able to change the orientation of the tip rigid part 116 in an up, down, left, or right direction by causing the bending part 114 to bend by operating the handheld operation section 102. The tip rigid part 116 is provided with an imaging optical system 130 (an imaging unit), an illumination unit 123, a forceps port 126, and so forth (see FIG. 1 to FIG. 3).

During observation or treatment, an operation of an operation unit 208 (see FIG. 2) enables white light and/or narrow-band light (one or more of red narrow-band light, green narrow-band light, and blue narrow-band light) to be radiated from illumination lenses 123A and 123B of the illumination unit 123. In addition, an operation of the air/water supply button 141 enables washing water to be ejected from a water supply nozzle that is not illustrated, so that an imaging lens 132 (an imaging lens) of the imaging optical system 130 and the illumination lenses 123A and 123B can be washed. The forceps port 126 opening in the tip rigid part 116 communicates with a pipe line that is not illustrated, so that a treatment tool that is not illustrated and is for extirpating a tumor or the like can be inserted into the pipe line and necessary treatment can be given to a subject by moving the treatment tool forward or backward as appropriate.

Figure 3:
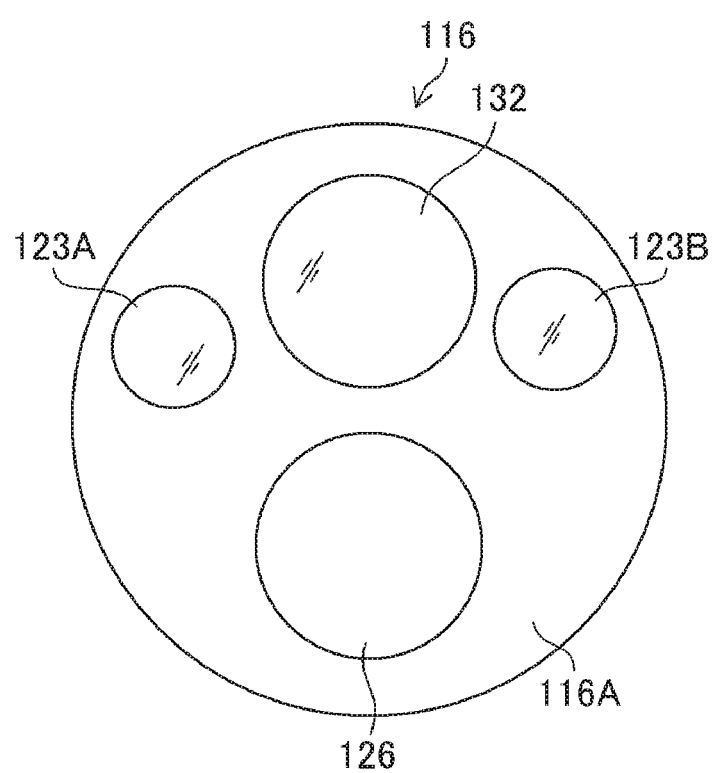
FIG. 3 is a diagram illustrating the configuration of a tip rigid part of an endoscope.

As illustrated in FIG. 1 to FIG. 3, the imaging lens 132 (an imaging unit) is disposed on a distal-end-side surface 116A of the tip rigid part 116. An imaging device 134 (an imaging device, an imaging unit) of a complementary metal-oxide semiconductor (CMOS) type, a driving circuit 136, and an analog front end (AFE) 138 are disposed behind the imaging lens 132, and these elements output an image signal. The imaging device 134 is a color imaging device and includes a plurality of pixels constituted by a plurality of light-receiving elements arranged in a matrix (arranged two-dimensionally) in a specific pattern arrangement (Bayer arrangement, X-Trans (registered trademark) arrangement, honeycomb arrangement, or the like). Each pixel of the imaging device 134 includes a microlens, a red (R), green (G), or blue (B) color filter, and a photoelectric conversion unit (a photodiode or the like). The imaging optical system 130 is capable of generating a color image from pixel signals of three colors, red, green, and blue, and is also capable of generating an image from pixels signals of any one or two colors among red, green, and blue. In the first embodiment, a description will be given of a case where the imaging device 134 is a CMOS-type imaging device, but the imaging device 134 may be of a charge coupled device (CCD) type. Each pixel of the imaging device 134 may further include a purple color filter corresponding to a purple light source and/or an infrared filter corresponding to an infrared light source.

An optical image of a subject (a tumor portion, a lesion portion) is formed on a light-receiving surface (an imaging surface) of the imaging device 134 by the imaging lens 132, converted into an electric signal, output to the processor 200 through a signal cable that is not illustrated, and converted into a video signal. Accordingly, an observation image is displayed on the monitor 400, which is connected to the processor 200.

The illumination lenses 123A and 123B of the illumination unit 123 are provided next to the imaging lens 132 on the distal-end-side surface 116A of the tip rigid part 116. An emission end of a light guide 170, which will be described below, is disposed behind the illumination lenses 123A and 123B. The light guide 170 extends through the insertion section 104, the handheld operation section 102, and a universal cable 106, and an incidence end of the light guide 170 is located in a light guide connector 108.

Configuration of Light Source Apparatus

As illustrated in FIG. 2, the light source apparatus 300 is constituted by a light source 310 for illumination, a diaphragm 330, a condenser lens 340, a light source control unit 350, and so forth, and causes observation light to enter the light guide 170. The light source 310 includes a red light source 310R, a green light source 310G, and a blue light source 310B that emit red narrow-band light, green narrow-band light, and blue narrow-band light, respectively, and is capable of radiating red narrow-band light, green narrow-band light, and blue narrow-band light. The illuminance of observation light from the light source 310 is controlled by the light source control unit 350, which is capable of decreasing the illuminance of observation light or stopping illumination as necessary.

The light source 310 is capable of emitting red narrow-band light, green narrow-band light, and blue narrow-band light in any combination. For example, the light source 310 is capable of simultaneously emitting red narrow-band light, green narrow-band light, and blue narrow-band light to radiate white light (normal light) as observation light, and is also capable of emitting any one or two of red narrow-band light, green narrow-band light, and blue narrow-band light to radiate narrow-band light (special light). The light source 310 may further include a purple light source that radiates purple light (an example of narrow-band light) and/or an infrared light source that radiates infrared light (an example of narrow-band light). Alternatively, with use of a light source that radiates white light and a filter that allows white light and each narrow-band light to pass therethrough, white light or narrow-band light may be radiated as observation light (see, for example, FIGS. 20 to 22B).

Wavelength Range of Light Source

The light source 310 may be a light source that generates light in a white range or light in a plurality of wavelength ranges as the light in the white range, or may be a light source that generates light in a specific wavelength range narrower than the white wavelength range. The specific wavelength range may be a blue range or green range in a visible range, or may be a red range in the visible range. In a case where the specific wavelength range is the blue range or green range in the visible range, the specific wavelength range may include a wavelength range of 390 nm or more and 450 nm or less or a wavelength range of 530 nm or more and 550 nm or less, and the light in the specific wavelength range may have a peak wavelength in the wavelength range of 390 nm or more and 450 nm or less or the wavelength range of 530 nm or more and 550 nm or less. In a case where the specific wavelength range is the red range in the visible range, the specific wavelength range may include a wavelength range of 585 nm or more and 615 nm or less or a wavelength range of 610 nm or more and 730 nm or less, and the light in the specific wavelength range may have a peak wavelength in the wavelength range of 585 nm or more and 615 nm or less or the wavelength range of 610 nm or more and 730 nm or less.

The above-described specific wavelength range may include a wavelength range in which a light absorption coefficient is different between oxyhemoglobin and deoxyhemoglobin, and the light in the specific wavelength range may have a peak wavelength in the wavelength range in which the light absorption coefficient is different between oxyhemoglobin and deoxyhemoglobin. In this case, the specific wavelength range may include a wavelength range of 400±10 nm, a wavelength range of 440±10 nm, a wavelength range of 470±10 nm, or a wavelength range of 600 nm or more and 750 nm or less, and the light in the specific wavelength range may have a peak wavelength in the wavelength range of 400±10 nm, the wavelength range of 440±10 nm, the wavelength range of 470±10 nm, or the wavelength range of 600 nm or more and 750 nm or less.

The wavelength range of the light generated by the light source 310 may include a wavelength range of 790 nm or more and 820 nm or less or a wavelength range of 905 nm or more and 970 nm or less, and the light generated by the light source 310 may have a peak wavelength in the wavelength range of 790 nm or more and 820 nm or less or the wavelength range of 905 nm or more and 970 nm or less.

Alternatively, the light source 310 may include a light source that radiates excitation light whose peak is 390 nm or more and 470 nm or less. In this case, a medical image (an inside-of-living-body image) having information about fluorescence emitted by a fluorescent substance in a subject (a living body) can be acquired. In the case of acquiring a fluorescence image, a pigment for a fluorescence method (fluorescein, acridine orange, or the like) may be used.

It is preferable that the type of the light source 310 (a laser light source, a xenon light source, a light-emitting diode (LED) light source, or the like), the wavelength of the light source 310, the presence or absence of a filter for the light source 310, and so forth be determined in accordance with the type of photographic subject, the purpose of observation, or the like. It is also preferable that, during observation, the wavelengths of observation light be combined and/or switched in accordance with the type of photographic subject, the purpose of observation, or the like. In the case of switching the wavelength, for example, a disc-shaped filter (a rotary color filter) that is disposed in front of the light source and that is provided with a filter for transmitting or blocking light of a specific wavelength may be rotated to switch the wavelength of light to be radiated (see FIGS. 20 to 22B).

The imaging device used to carry out the present invention is not limited to a color imaging device in which color filters are disposed for the individual pixels, such as the imaging device 134, and may be a monochrome imaging device. In the case of using a monochrome imaging device, imaging can be performed in a frame sequential (color sequential) manner by sequentially switching the wavelength of observation light. For example, the wavelength of outgoing observation light may be sequentially switched among blue, green, and red, or wide-band light (white light) may be radiated and the wavelength of outgoing observation light may be switched by using a rotary color filter (red, green, blue, and the like). Alternatively, one or a plurality of types of narrow-band light (green, blue, and the like) may be radiated and the wavelength of outgoing observation light may be switched by using a rotary color filter (green, blue, and the like). The narrow-band light may be infrared light of two or more different wavelengths (first narrow-band light and second narrow-band).

As a result of connecting the light guide connector 108 (see FIG. 1) to the light source apparatus 300, observation light radiated by the light source apparatus 300 is transmitted through the light guide 170 to the illumination lenses 123A and 123B and is radiated from the illumination lenses 123A and 123B to an observation range.

Configuration of Processor

The configuration of the processor 200 will be described with reference to FIG. 2. In the processor 200, an image input controller 202 receives an image signal output from the endoscope main body 100, an image processing unit 204 performs necessary image processing thereon, and a video output unit 206 outputs a resulting image signal. Accordingly, an observation image (an inside-of-living-body image) is displayed on the monitor 400 (a display apparatus). These processing operations are performed under control by a central processing unit (CPU) 210. Specifically, the CPU 210 has functions as an image acquiring unit, a mode control unit, a specific target detecting unit, a region-of-interest detecting unit, a classifying unit, a display control unit, a detector, a ratio setting unit, a parameter calculating unit, and an image generating unit. A communication control unit 205 controls communication with a hospital information system (HIS), a hospital local area network (LAN), and the like that are not illustrated. In a recording unit 207, an image of a photographic subject (a medical image, a captured image), information indicating a result of detection and/or classification of a region of interest, and the like are recorded. An audio processing unit 209 outputs a message (sound) or the like based on the result of detection and/or classification of the region of interest from a speaker 209A under control by the CPU 210 and the image processing unit 204.

A read only memory (ROM) 211 is a nonvolatile storage element (a non-transitory recording medium) and stores a computer-readable code of a program that causes the CPU 210 and/or the image processing unit 204 (an image processing apparatus, a computer) to execute the image processing method according to the present invention. A random access memory (RAM) 212 is a storage element for temporary storage in various processing operations and can be used as a buffer when acquiring an image.

Functions of Image Processing Unit

Figure 4:
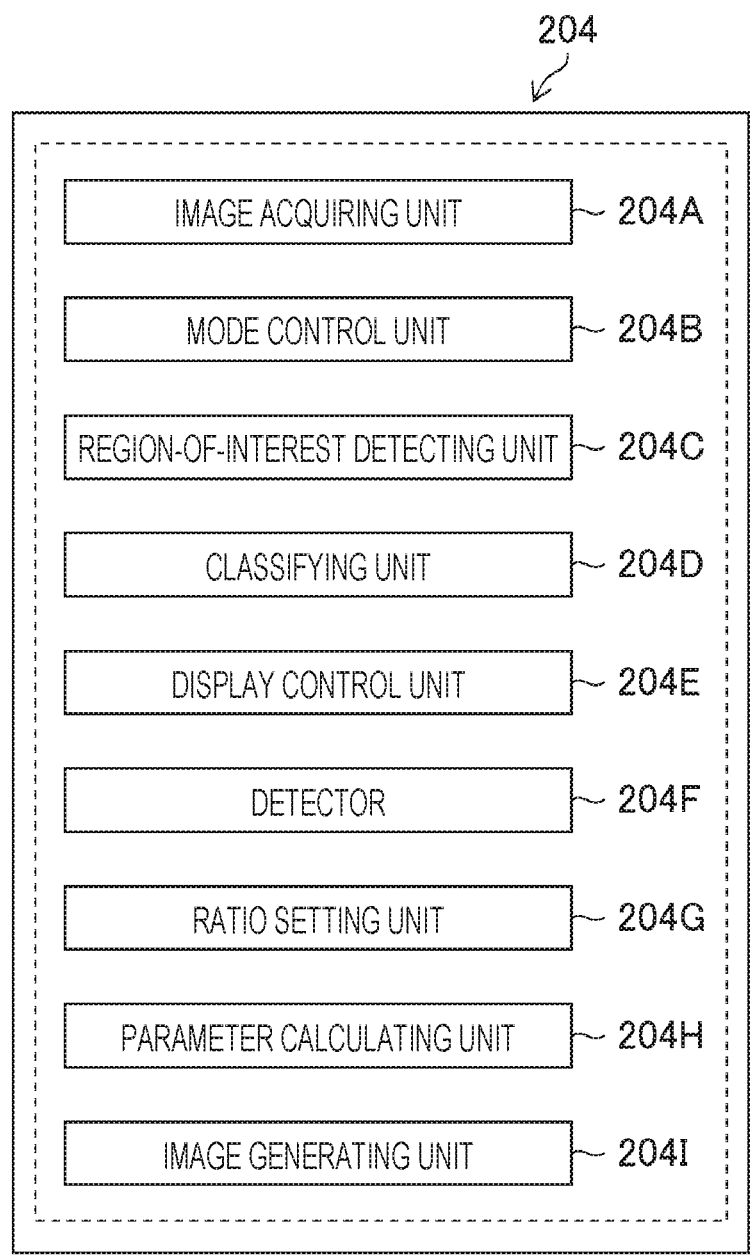
FIG. 4 is a diagram illustrating a functional configuration of an image processing unit.

FIG. 4 is a diagram illustrating a functional configuration of the image processing unit 204 (a medical image acquiring unit, a medical image analysis processing unit, a medical image analysis result acquiring unit). The image processing unit 204 has an image acquiring unit 204A (an image acquiring unit), a mode control unit 204B (a mode control unit), a region-of-interest detecting unit 204C (a specific target detecting unit, a region-of-interest detecting unit), a classifying unit 204D (a classifying unit), a display control unit 204E (a display control unit), a detector 204F (a specific target detecting unit, a detector), a ratio setting unit 204G (a ratio setting unit), a parameter calculating unit 204H (a parameter calculating unit), and an image generating unit 204I (an image generating unit). The region-of-interest detecting unit 204C, the detector 204F, and the classifying unit 204D also operate as a medical image analysis processing unit.

In addition, the image processing unit 204 may include a special-light image acquiring unit that acquires a special-light image having information about a specific wavelength range on the basis of a normal-light image that is acquired by radiating light in the white range or light in a plurality of wavelength ranges as the light in the white range. In this case, a signal in the specific wavelength range can be acquired through computation based on color information of RGB (R: red, G: green, B: blue) or CMY (C: cyan, M: magenta, Y: yellow) included in the normal-light image.

In addition, the image processing unit 204 may include a feature quantity image generating unit that generates a feature quantity image through computation based on at least one of a normal-light image that is acquired by radiating light in the white range or light in a plurality of wavelength ranges as the light in the white range or a special-light image that is acquired by radiating light in a specific wavelength range, and may acquire and display the feature quantity image as a medical image.

The processing operations using these functions of the image processing unit 204 will be described in detail below. The processing operations using these functions are performed under control by the CPU 210.

The above-described functions of the image processing unit 204 can be implemented by using various types of processors. The various types of processors include, for example, a central processing unit (CPU) which is a general-purpose processor that executes software (program) to implement various functions. Also, the various types of processors include a graphics processing unit (GPU) which is a processor dedicated to image processing, and a programmable logic device (PLD) which is a processor whose circuit configuration is changeable after manufacturing, such as a field programmable gate array (FPGA). Furthermore, the various types of processors include a dedicated electric circuit which is a processor having a circuit configuration designed exclusively for executing specific processing, such as an application specific integrated circuit (ASIC).

The function of each unit may be implemented by one processor or may be implemented by a plurality of processors of the same type or different types (for example, a combination of a plurality of FPGAs, a combination of a CPU and an FPGA, or a combination of a CPU and a GPU). A plurality of functions may be implemented by one processor. A first example of implementing a plurality of functions by one processor is that a combination of one or more CPUs and software constitute one processor and the one processor implements the plurality of functions, as represented by a computer, such as a main body of an image processing apparatus or a server. A second example is that a processor that implements the functions of an entire system by one integrated circuit (IC) chip is used, as represented by a system on chip (SoC). In this way, various functions are configured as a hardware structure by using one or more of the above-described various types of processors. Furthermore, the hardware structure of the various types of processors is, more specifically, electric circuitry formed by combining circuit elements such as semiconductor elements.

When the above-described processor or electric circuitry executes the software (program), a processor (computer)-readable code of the software to be executed is stored in a non-transitory recording medium, such as a read only memory (ROM), and the processor refers to the software. The software stored in the non-transitory recording medium includes a program for executing input of an image and measurement of a photographic subject. The code may be recorded on a non-transitory recording medium, such as a magneto-optical recording device of various types or a semiconductor memory, instead of the ROM. In the processing using the software, a random access memory (RAM) may be used as a transitory storage region, for example, and data stored in an Electronically Erasable and Programmable Read Only Memory (EEPROM) that is not illustrated can be referred to, for example.

Configuration of Operation Unit

The processor 200 includes the operation unit 208. The operation unit 208 includes an operation mode setting switch or the like that is not illustrated and is capable of setting the wavelength of observation light (white light or narrow-band light, which narrow-band light is to be used in the case of narrow-band light). In addition, the operation unit 208 includes a keyboard and a mouse that are not illustrated. A user is able to perform operations of setting an imaging condition and a display condition via these devices. These setting operations may be performed via a foot switch that is not illustrated, or may be performed by using a voice, a line of sight, a gesture, or the like. The setting of an operation mode may be performed by allocating an operation mode setting function to the function button 143 of the handheld operation section 102 (see FIG. 1) as described above. In addition, the user is able to perform an operation of setting a "first ratio" in a first image acquisition mode and a "second ratio" in a second image acquisition mode via the operation unit 208. Furthermore, the user is able to set termination conditions of the first image acquisition mode and the second image acquisition mode (a first termination condition and a second termination condition: setting of an elapsed time, the number of acquired still images, or the like) and provide a termination instruction via the operation unit 208.

Configuration of Recording Unit

The rescoring unit 207 (a recording device) is configured including a non-transitory recording medium, such as a magneto-optical recording medium of various types or a semiconductor memory, and a control unit for the recording medium, and stores a captured image (a first image, a second image), an alignment first image, information indicating a region of interest, a classification result of the region of interest, information indicating a detection result of an agent and/or equipment, and the like in association with each other. These images and information are displayed on the monitor 400 as a result of an operation performed via the operation unit 208 and control by the CPU 210 and/or the image processing unit 204.

In addition to the above-described images, an analysis result about either or both of a region of interest (a region of concern), which is a region to be focused on included in a medical image, and the presence or absence of a target to be focused on may be recorded in the recording unit 207 (a recording device). In this case, the image processing unit 204 (a medical image analysis processing unit, a medical image analysis result acquiring unit) is capable of acquiring the analysis result from the recording unit 207 and displaying the analysis result on the monitor 400.

Configuration of Display Apparatus

The monitor 400 (a display apparatus) displays a first image, a second image, an alignment first image, an imaging condition setting screen, a display condition setting screen, information indicating a detection result of a region of interest, information indicating a classification result of the region of interest, information indicating a detection result of an agent and/or equipment, and the like, as a result of an operation performed via the operation unit 208 and control by the CPU 210 and/or the image processing unit 204. The monitor 400 has a touch panel that is not illustrated and that is for performing an imaging condition setting operation and/or a display condition setting operation.

Image Processing Method

Processing in a Case where Specific Target is Region of Interest

Figure 5:
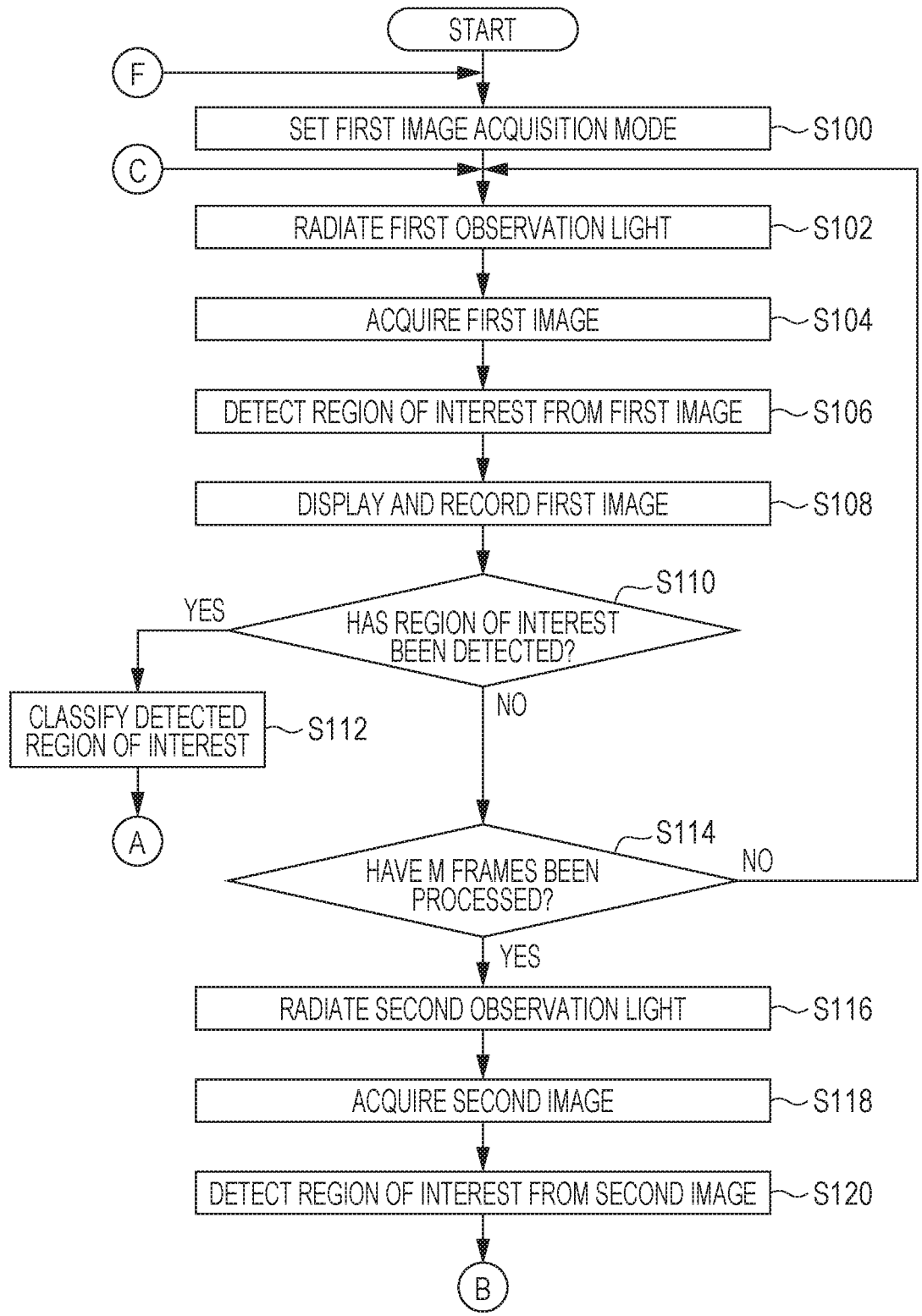
FIG. 5 is a flowchart illustrating processing in the case of detecting a region of interest.
Figure 6:
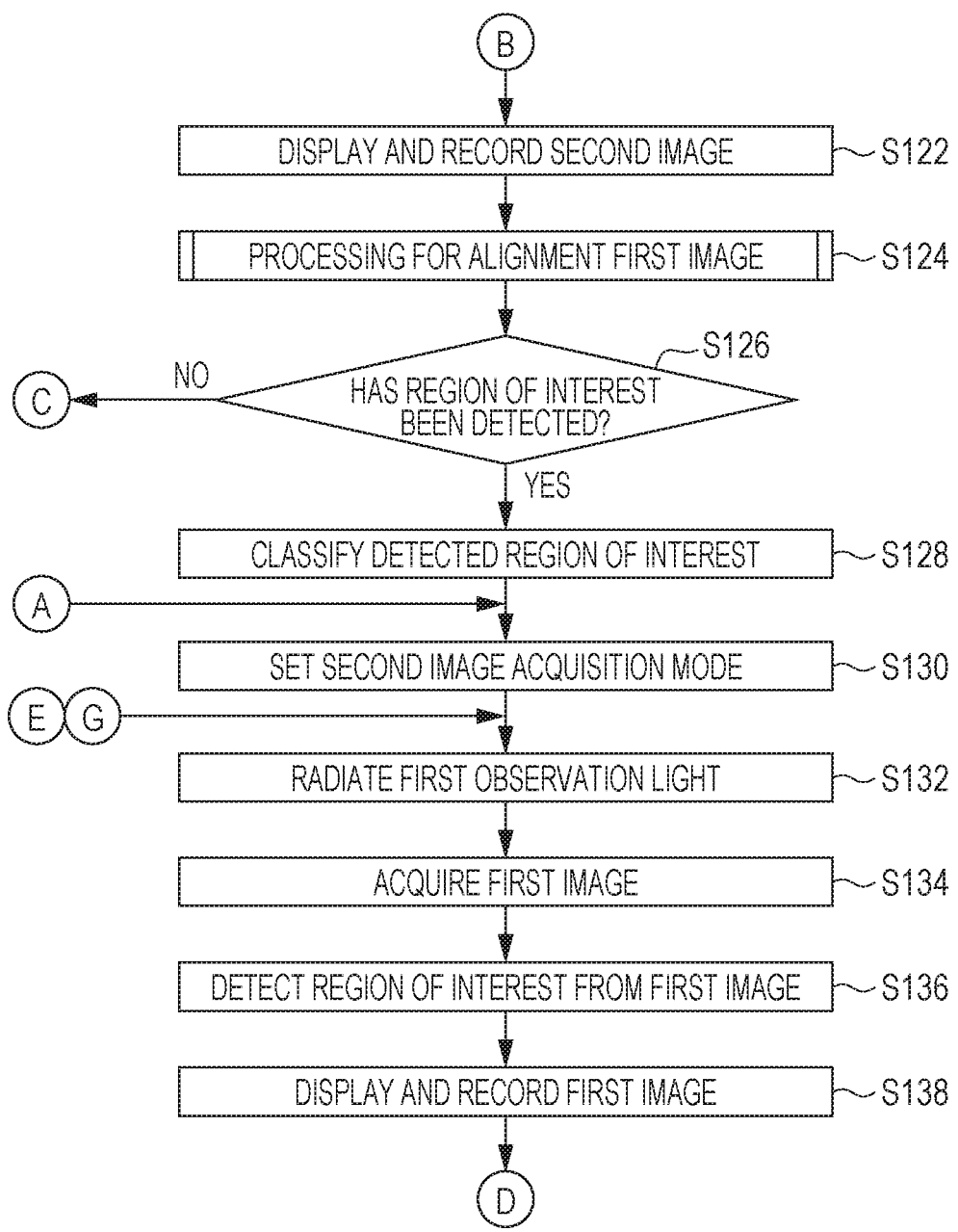
FIG. 6 is a flowchart (continued from FIG. 5) illustrating the processing in the case of detecting a region of interest.
Figure 7:
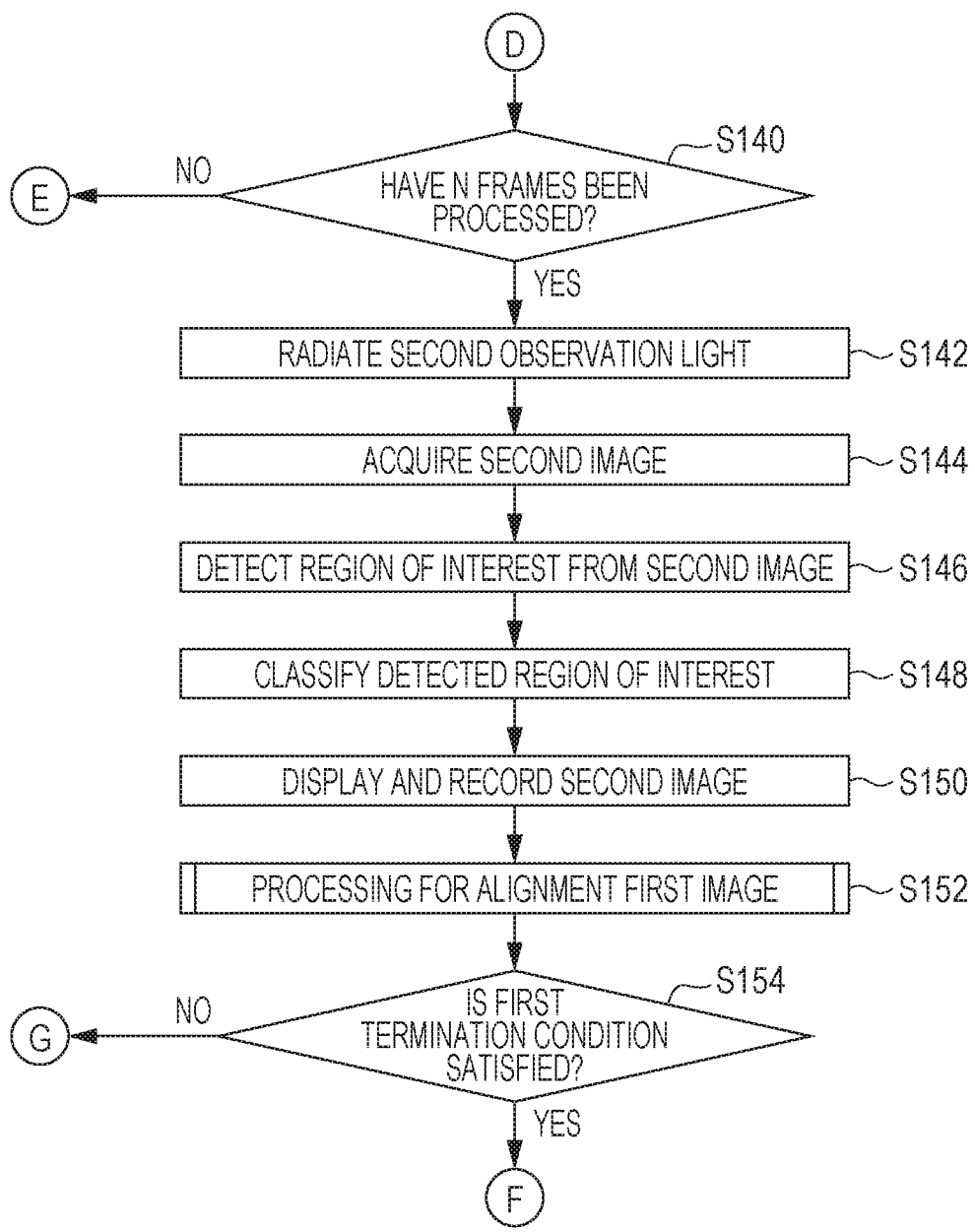
FIG. 7 is a flowchart (continued from FIG. 6) illustrating the processing in the case of detecting a region of interest.

An image processing method using the endoscope system 10 having the above-described configuration will be described. FIGS. 5 to 7 are flowcharts illustrating the processing of an image processing method according to the first embodiment (in a case where a specific target is a region of interest).

Observation Light of First Image and Second Image

In the first embodiment, a description will be given of a case where a white-light image (a normal-light image) using white light as observation light (first observation light) is acquired as a first image and a blue-light image (a special-light image) using blue light which is narrow-band light (the center wavelength is shorter than that of the first observation light) as observation light (second observation light) is acquired as a second image. However, in the present invention, the observation light is not limited to such a combination. For example, the second image may be a special-light image acquired by using green light, red light, infrared light, purple light, or the like which is a narrow-band light as observation light. Alternatively, a first image and a second image may be acquired by using first observation light and second observation light each of which is narrow-band light (for example, first narrow-band light and second narrow-band light, such as blue light and green light or red light beams having different wavelengths). In the first embodiment, it is assumed that a first image and a second image are captured by radiating only first observation light or only second observation light in one frame.

Acquisition Patterns of First Image and Second Image

Figure 8A:
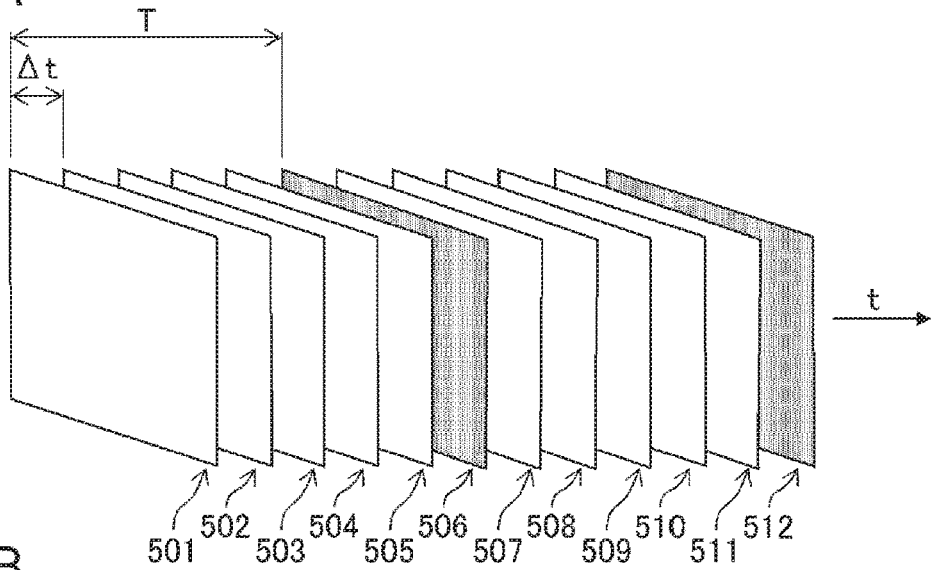
FIGS. 8A to 8C are diagrams illustrating examples of a pattern of acquiring a first image and a second image.
Figure 8B:
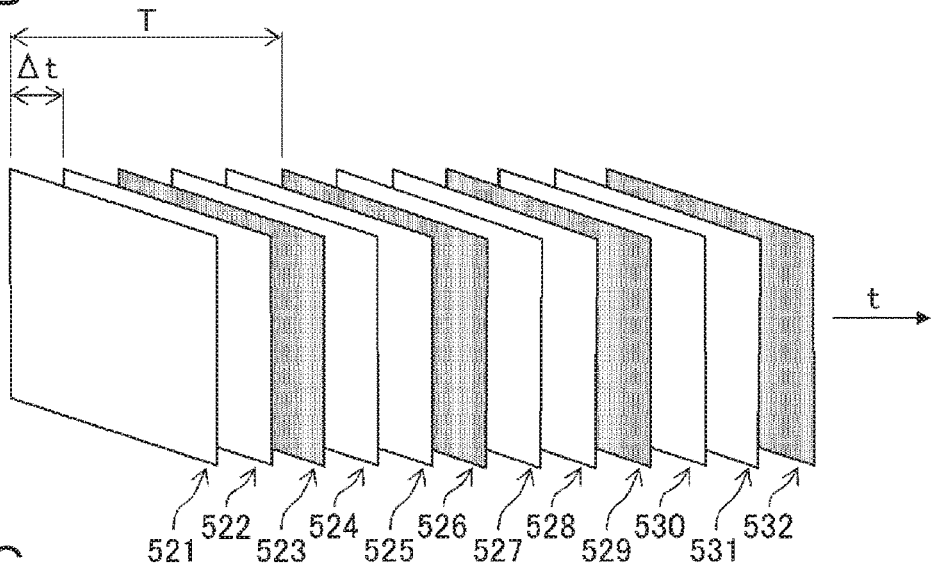
Figure 8C:
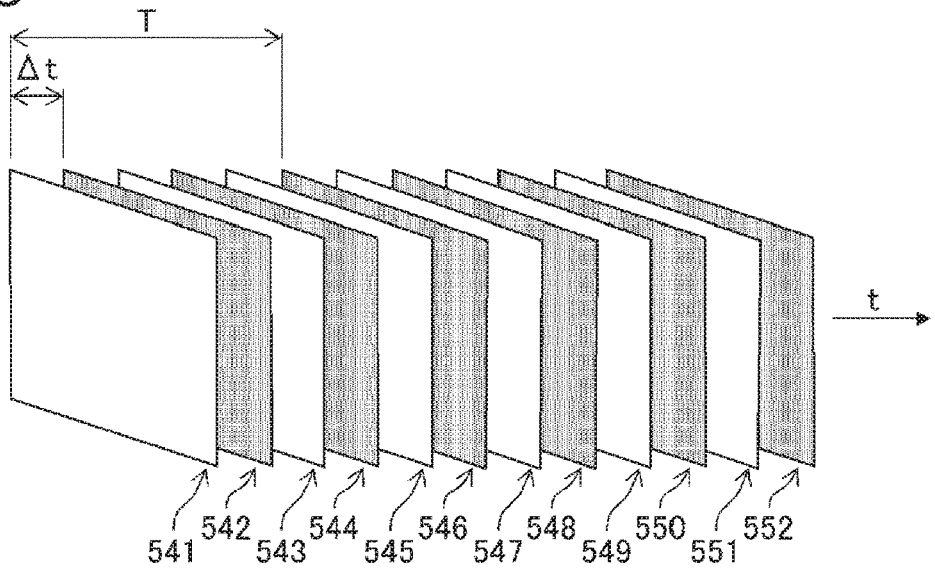
Figure 9:
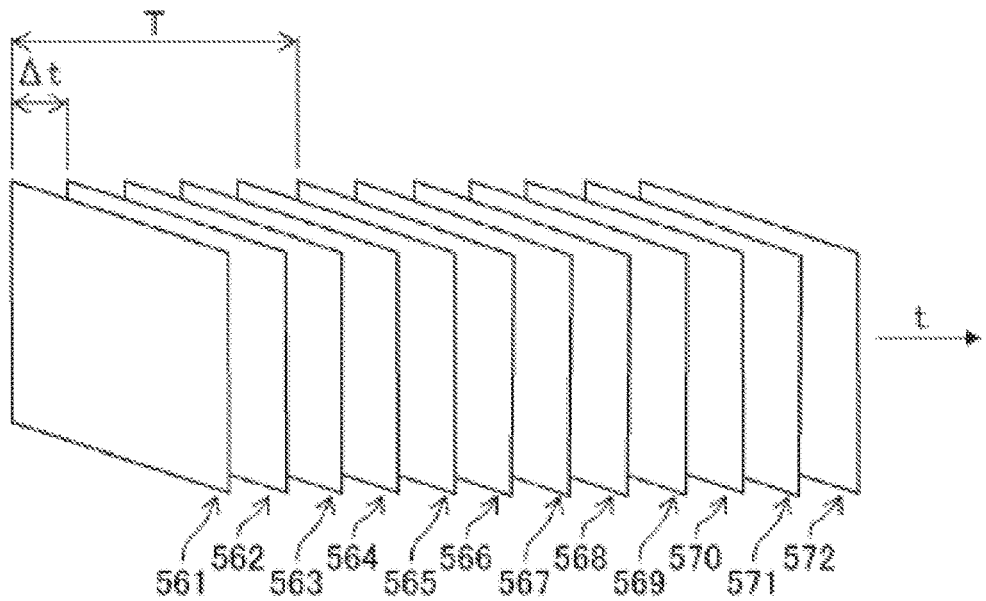
FIG. 9 is a diagram illustrating an example of a pattern of acquiring a first image and a second image.

FIGS. 8A to 9 are diagrams illustrating examples of an acquisition pattern of a first image and a second image according to the first embodiment. Each of these figures illustrates a state in which images are acquired from the left to the right in the figure along a time axis t. FIG. 8A illustrates a pattern in which first observation light (white light, normal light) is continuously radiated for five frames at a designated frame rate (a frame interval: $\Delta t$), for example, 30 frames or 60 frames per second, to capture five white-light images (images 501 to 505, 507 to 511), and then second observation light (blue narrow-band light, special light) is radiated for one frame to capture one blue-light image (image 506, 512). In this pattern, the white-light image and the blue-light image are images captured at different times. FIG. 8B illustrates a pattern in which first observation light (white light, normal light) is continuously radiated for two frames to capture two white-light images (images 521 and 522, 524 and 525, 527 and 528, 530 and 531), and then second observation light (blue narrow-band light, special light) is radiated for one frame to capture one blue-light image (image 523, 526, 529, 532). Also in this pattern, the white-light image and the blue-light image are images captured at different times. FIG. 8C illustrates a pattern in which first observation light (white light, normal light) and second observation light (blue narrow-band light, special light) are alternately radiated. Accordingly, white-light images (images 541, 543, 545, 547, 549, and 551) and blue-light images (images 542, 544, 546, 548, 550, and 552) are alternately acquired.

In the first image acquisition mode and the second image acquisition mode, a pattern can be selected from among patterns including, in addition to the patterns illustrated in FIGS. 8A to 8C, other patterns in which the second image acquisition ratio is different. Note that the second image acquisition ratio in the second image acquisition mode (a second ratio: the ratio of the number of acquired frames of a second image to the number of acquired frames of a first image in a predetermined time range) is higher than the second image acquisition ratio in the first image acquisition mode (a first ratio: the ratio of the number of acquired frames of a second image to the number of acquired frames of a first image in the predetermined time range). For example, the pattern illustrated in FIG. 8A can be regarded as the first image acquisition mode, and the pattern illustrated in FIG. 8B can be regarded as the second image acquisition mode. In this case, in the pattern illustrated in FIG. 8A, the ratio of the number of acquired frames of a second image to the number of acquired frames of a first image in a time range T (a first ratio) is 1/5 (1:5), whereas in the pattern illustrated in FIG. 8B, the ratio of the number of acquired frames of a second image to the number of acquired frames of a first image in the time range T (a second ratio) is 1/2 (1:2). The setting of such an imaging pattern in the first image acquisition mode and the second image acquisition mode (specifically, the first ratio and/or the second ratio) can be performed by, for example, the ratio setting unit 204G in accordance with a user operation via the operation unit 208. Note that the second image acquisition ratio can be set in accordance with a user operation or the like but the mode control unit 204B does not set a pattern in which a second image is acquired in all frames and a first image is not acquired at all.

In the first image acquisition mode, a pattern in which only first observation light is radiated as in FIG. 9 can be adopted (a second image is not acquired and thus the second image acquisition mode is not available), in addition to the patterns in which first observation light (white light, normal light) and second observation light (blue narrow-band light, special light) are radiated as in FIGS. 8A to 8C. In the case of the pattern illustrated in FIG. 9, the ratio of the number of acquired frames of a second image to the number of acquired frames of a first image in the time range T (a first ratio) is zero (0:5). In the case of using the pattern illustrated in FIG. 9 in the first image acquisition mode, if any one of the patterns illustrated in FIGS. 8A to 8C is used in the second image acquisition mode, the second ratio is higher than the first ratio.

Processing in a Case where Specific Target is Region of Interest

FIGS. 5 to 7 illustrate the processing in a case where a specific target is a region of interest. In this case, the region-of-interest detecting unit 204C (a specific target detecting unit) detects a region of interest as a specific target. In an initial state (a state in which a region of interest has not been detected), the mode control unit 204B sets the image acquiring unit 204A to the first image acquisition mode (step S100: a mode control step), so that the display frame rate of a first image (a white-light image, a normal-light image) does not decrease.

Acquisition of Image in First Image Acquisition Mode

Processing for First Image

The image acquiring unit 204A controls the light source control unit 350 in the first image acquisition mode (the pattern illustrated in FIG. 8A) to cause the red light source 310R, the green light source 310G, and the blue light source 310B to emit light and irradiate a subject with white light (first observation light) (step S102: an imaging step, an image acquisition step), and the imaging optical system 130, the imaging device 134, and so forth capture an image (a first image, a normal-light image) of the subject (step S104: an imaging step, an image acquisition step). The captured image is acquired by (input to) the image acquiring unit 204A via the image input controller 202 (step S104: an image acquisition step).

Detection of Region of Interest

The region-of-interest detecting unit 204C (a specific target detecting unit) detects a region of interest from the acquired first image (step S106: a specific target detection step, a region-of-interest detection step). Detection of a region of interest can be performed by the region-of-interest detecting unit 204C that includes, for example, a known computer aided diagnosis (CAD) system. Specifically, for example, a region of interest (a region of interest which is a region to be focused on) and the presence or absence of a target (a target to be focused on) in the region of interest can be extracted on the basis of a feature quantity of pixels of a medical image. In this case, the region-of-interest detecting unit 204C divides a detection target image into a plurality of rectangular regions, for example, and sets the individual rectangular regions obtained through division as local regions. The region-of-interest detecting unit 204C calculates, for each local region of the detection target image, a feature quantity (for example, a hue) of the pixels in the local region, and determines a local region having a specific hue among the local regions to be a region of interest. In step S106, "detects a region of interest" means "performs detection processing on an image".

Detection of Region of Interest Based on Deep Learning Algorithm

Detection of a region of interest may be performed by using a result of deep learning. For example, every time a new image is recorded in the recording unit 207 (or every time a new image is captured), the region-of-interest detecting unit 204C performs image analysis processing using deep learning on the basis of a deep learning algorithm, thereby analyzing whether or not the image includes a region of interest. The deep learning algorithm is an algorithm of recognizing whether or not the image includes a region of interest by using a known method of a convolutional neural network, that is, repetition of a convolutional layer and a pooling layer, a fully connected layer, and an output layer. The image analysis processing using deep learning may use a learner generated by giving images labeled with "is a region of interest" or "is not a region of interest" as training data. "Whether or not to perform such machine learning" and/or "whether or not to use a learning result" may be set in accordance with a user operation via the operation unit 208 and the monitor 400.

Examples of a region of interest (a region of concern) detected in step S106 may include a polyp, a cancer, a colon diverticulum, an inflammation, a treatment scar (a scar of endoscopic mucosal resection (EMR), a scar of endoscopic submucosal dissection (ESD), a clip portion, or the like), a bleeding point, a perforation, angiodysplasia, and the like.

Display and Recording of First Image

The region-of-interest detecting unit 204C and the display control unit 204E perform output (display, recording) about a white-light image (a first image) (step S108: a display control step, a recording step). The output can be performed such that the display control unit 204E, the region-of-interest detecting unit 204C, and the classifying unit 204D display the white-light image (the first image), information indicating a detection result, and information indicating a classification result on the monitor 400 (a display control step) and record these pieces of information in the recording unit 207 (a recording step). The region-of-interest detecting unit 204C and the classifying unit 204D may output information indicating a detection result of a region of interest as a sound via the audio processing unit 209 and the speaker 209A. A display example of a first image will be described below. While a first image (and an alignment first image described below) is continuously recorded as a moving image, a frame in which a region of interest has been detected may be recorded as a still image.

The region-of-interest detecting unit 204C determines whether or not a region of interest has been detected (step S110). If a region of interest has been detected, the processing proceeds to step S112, where the classifying unit 204D classifies the region of interest. Subsequently, the processing proceeds to step S130, where the mode control unit 204B sets the image acquiring unit 204A to the second image acquisition mode. If a region of interest has not been detected (NO in step S110), the processing proceeds to step S114, where the image acquiring unit 204A repeats first image acquisition processing for M frames (while the determination in step S114 is NO). In a case where the first image acquisition mode is the pattern illustrated in FIG. 8A, M=5. After the first image acquisition processing for M frames has finished, the processing proceeds to step S116.

Classification of Region of Interest

If a region of interest has been detected, the classifying unit 204D classifies the detected region of interest (step S112: a region-of-interest classification step). Examples of classification may be classification of a polyp (neoplastic or non-neoplastic), diagnosis of the stage of cancer, a current position in a lumen (a pharynx, an esophagus, a stomach, a duodenum, or the like in an upper portion; a cecum, an ascending colon, a transverse colon, a descending colon, a sigmoid colon, a rectum, or the like in a lower portion), and the like. In the classification, a result of machine learning (deep learning) can be used as in the case of detection. The classification of the region of interest may be performed together with detection. In a case where the first observation light is white light and the second observation light is blue narrow-band light, it is preferable that the classifying unit 204D classify the region of interest on the basis of at least a second image of a first image and a second image. This is because, in the above-described example, the second image is captured by using blue narrow-band light whose center wavelength is shorter than that of the first observation light (white light) and is suitable for classifying a minute structure of a lesion or the like. The image to be used to classify the region of interest may be set on the basis of a user operation performed via the operation unit 208 or may be set by the classifying unit 204D without a user operation.

An image in which a region of interest, such as a lesion, has been detected (hereinafter referred to as a "lesion image") may be stored (recorded) in association with a test in which a specific lesion (a lesion of low prevalence, a case difficult to be detected, or the like) has been found. For example, in a case where the size of a lesion is small or in a case where the shape of a lesion is flat and hardly has a bump, a lesion image (a still image, a moving image) can be stored as a "lesion difficult to be detected". For example, in a case where pathological biopsy is performed (in this case, it is considered "a lesion subjected to biopsy is difficult to be determined by endoscopic findings") or in a case where a result of pathological biopsy does not match endoscopic findings (for example, biopsy is performed because of endoscopic findings "suspected adenoma" but a pathological result is a hyperplastic polyp), a lesion image can be stored as a "lesion difficult to be diagnosed". Furthermore, in the case of constructing a learner through machine learning by using a lesion image as an input, the lesion mage may be stored in accordance with the usage purpose of the learner. For example, in the case of constructing a learner aimed at detecting (picking out) a lesion in screening, only a test aimed at screening may be stored (manipulation video of endoscopic submucosal dissection (ESD) or the like is of low utility value in machine learning or the like), and in the case of constructing a leaner aimed at determining the stage of cancer (intramucosal cancer, advanced cancer, or the like), only a lesion image of a test aimed at treatment, such as ESD or endoscopic mucosal resection (EMR), may be stored.

Processing for Second Image

In a case where the first ratio is not zero in the first image acquisition mode (in a case where the image acquisition pattern is the pattern illustrated in any one of FIGS. 8A to 8C, for example), processing for a second image is performed after processing for a first image has been performed on M frames (YES in step S114). The processing for a second image in step S116 to step S122 is similar to the above-described processing for a first image in step S102 to step S108 except that the wavelength of the observation light is different (in the above-described example, the first observation light is white light and the second observation light is blue narrow-band light). Specifically, the processing from step S116 to step S122 (an image acquisition step, a mode control step, a specific target detection step, a region-of-interest classification step, and an output step) can be performed by controlling the individual units of the image processing unit 204 (the image acquiring unit 204A, the region-of-interest detecting unit 204C, the classifying unit 204D, and so forth).

In a case where the second observation light is blue light (the center wavelength is shorter than that of white light), the second image depicts the structure of minute blood vessels or the like with high contrast and thus a region of interest can be detected and classified with high accuracy. Thus, the second image can be used by being input to a learner and classified or by being recorded as a training image. It is therefore preferable that the classifying unit 204D classify the region of interest on the basis of at least one of the first image and the second image. In the first embodiment, the first image (a normal-light image) is continuously displayed on the monitor 400. Thus, the second image or a detection result and a classification result for the second image may be output (displayed, recorded, and the like) as necessary (for example, when a user instruction is input via the operation unit 208 or when a region of interest (a specific target) satisfying a designated condition is detected) (step S122, and also steps S150, S320, and S344 described below).

The flowcharts in FIGS. 5 to 7 illustrate the processing in the case of acquiring a first image and a second image in the pattern illustrated in FIG. 8A in the first image acquisition mode (in a case where the first ratio is not zero). In a case where the first ratio is zero in the first image acquisition mode (in the case of the pattern illustrated in FIG. 9), the processing from step S102 to step S110 is repeated with the processing for the second image (step S114 to step S128) not being performed, and if a region of interest is detected from the first image (YES in step S110), the mode shifts to the second image acquisition mode (step S130).

Prevention of Decrease in Frame Rate of First Image

In the first embodiment, to prevent degradation of image quality resulting from wavelength separation, only the first observation light or the second observation light is radiated as observation light, and the first observation light and the second observation light are not simultaneously radiated, and thus a first image is not acquired at the radiation timing of the second observation light. For example, in the case of acquiring a first image and a second image in the pattern illustrated in FIG. 8A, a first image is not acquired at the acquisition timings of the images 506 and 512 (second images). Thus, in the first embodiment, an "alignment first image" ("a first image at the imaging time of a second image, generated by applying an alignment parameter to a first image") is generated and displayed in the manner described below to prevent a substantial decrease in the frame rate of the first image (step S124). The details of the processing of generating an alignment first image will be described below.

In step S126, the region-of-interest detecting unit 204C determines whether or not a region of interest has been detected from the second image. If the determination is affirmative, the classifying unit 204D classifies the region of interest (step S128). If the determination is negative, the processing returns to step S102, and the processing in the first image acquisition mode is repeated. As described above regarding the classification in the first image (step S112), in a case where the second image is captured by using blue narrow-band light whose center wavelength is shorter than that of the first observation light (white light), the second image is suitable for classifying a minute structure of a lesion or the like, and thus it is preferable to classify the region of interest on the basis of at least the second image.

Acquisition of Image in Second Image Acquisition Mode

If the region-of-interest detecting unit 204C (a specific target detecting unit, a region-of-interest detecting unit) has detected a region of interest, the mode control unit 204B causes the image acquiring unit 204A to acquire a first image and a second image in the second image acquisition mode until the first termination condition is satisfied (until a determination "YES" is obtained in step S154), and the processing from step S132 to step S154 is repeated. In the second image acquisition mode, a first image and a second image are acquired such that the ratio of the number of acquired frames of the second image to the number of acquired frames of the first image in the predetermined time range is the second ratio, which is higher than the first ratio. In a case where the first image acquisition mode is the imaging pattern illustrated in FIG. 8A (the first ratio: 1/5), the second image acquisition mode can be, for example, the imaging pattern illustrated in FIG. 8B (the second ratio: 1/2) or the imaging pattern illustrated in FIG. 8C (the second ratio: 1), but may be another pattern satisfying the condition for the ratio of the number of acquired frames of the second image (the second ratio is higher than the first ratio). In a case where the second image acquisition mode is the pattern illustrated in FIG. 8B (the second ratio: 1/2), the processing for a first image (step S132 to step S140) is performed for two frames (until N becomes 2 in step S140) and then the processing for a second image (step S142 to step S152) is performed for one frame. In this way, when a region of interest as a specific target is detected, the mode shifts to the second image acquisition mode, in which the second acquisition ratio is high, and thus an appropriate imaging mode can be set in accordance with the necessity for the second image.

Processing for First Image

In the second image acquisition mode, the processing of acquiring a first image and so forth (step S132 to step S138 in FIG. 6) can be performed similarly to the processing in the first image acquisition mode (step S102 to step S108), and thus the detailed description thereof is omitted.

Processing for Second Image

In step S140, the mode control unit 204B determines "whether or not N frames of the first image have been processed". For example, in the case of the imaging pattern illustrated in FIG. 8B, N is 2. When the processing for a first image (acquisition, detection of a region of interest, display of the image, and so forth) has been performed on N frames, the determination result in step S140 is YES, the second observation light is radiated under control by the image acquiring unit 204A and so forth, and a second image is acquired (steps S142 and S144). The processing of detecting a region of interest and so forth (step S146 to step S152) after the image has been acquired can be performed similarly to the above-described step S120 to step S124.

Setting of Image Acquisition Mode in Response to Satisfaction of Termination Condition The mode control unit 204B determines whether or not the first termination condition is satisfied (step S154). If the determination is affirmative, that is, if the first termination condition is satisfied, the processing returns to step S100, where the mode control unit 204B causes the image acquiring unit 204A to acquire a first image and a second image in the first image acquisition mode. Accordingly, an appropriate imaging mode can be set in accordance with the necessity for a second image to acquire the image, and a decrease in the frame rate of displaying the image (displaying the first image) can be prevented. The "first termination condition" may be, for example, elapse of a set time, acquisition of a designated number of still images (images of a region of interest or the like), no more detection of a region of interest, a termination instruction from a user, or the like, but is not limited to these examples. On the other hand, if the determination in step S154 is negative (if the first termination condition is not satisfied), the processing returns to step S132, where the mode control unit 204B continuously causes the image acquiring unit 204A to acquire a first image and a second image in the second image acquisition mode.

As described above, a first image and a second image are acquired, in the first image acquisition mode in a case where a specific target (a region of interest) has not been detected, and in the second image acquisition mode until the first termination condition is satisfied in a case where a specific target has been detected. Accordingly, images (a first image and a second image) can be acquired in an appropriate imaging mode based on a detection result, and processing using the second image suitable for discrimination, classification, and the like can be performed when a region of interest is detected while observation with the first image is continued.

Processing for Alignment First Image

Figure 10:
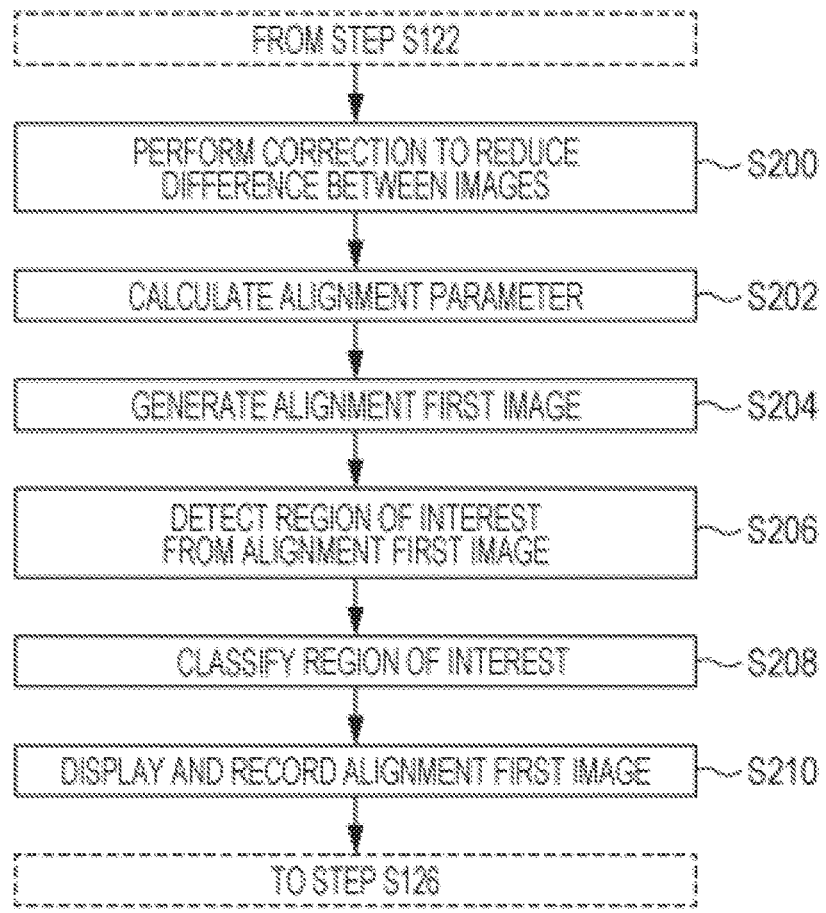
FIG. 10 is a diagram illustrating processing for an alignment first image.

Hereinafter, the details of the processing for an alignment first image in step S124 in FIG. 6 will be described with reference to the flowchart in FIG. 10. The processing in step S152 in FIG. 7 is similar thereto.

Image Used to Generate Alignment First Image

To generate an alignment first image, a first image (the image 525) acquired before a first image absence timing (an imaging timing of the image 526, which is a second image), for example, the image 525 (an example of a first image) and the image 526 (an example of a second image) in FIG. 8B, can be used. Other than this pattern, for example, a plurality of first images whose imaging times are different (in FIG. 8B, for example, the images 524 and 525) may be used, or a first image acquired after a first image absence timing (in FIG. 8B, for example, the image 527) may be used. However, in the case of using a first image captured at an imaging time after the imaging time of a second image, generation and display of an alignment first image may be delayed depending on a temporal difference in imaging time. In addition, in a case where a temporal difference in imaging time exceeds a threshold value, an imaging range, an imaging angle, or the like may be changed because of a motion of a photographic subject or the like, and the alignment accuracy may decrease.

In view of these circumstances, in generation of an alignment first image, it is preferable to use "a first image captured at an imaging time that is before an imaging time of a second image and that has a temporal difference smaller than or equal to the threshold value from the imaging time of the second image". Accordingly, an alignment first image can be generated with a small time delay and with a small change in the tint and structure of a photographic subject between frames. The threshold value for the imaging time can be determined in accordance with alignment accuracy, an allowable time for delay in generation and display of an image, and so forth. Hereinafter, a description will be given of the case of generating an alignment first image by using the image 525 as a first image and the image 526 as a second image.

Correction Before Alignment (Preprocessing)

Figure 11A:
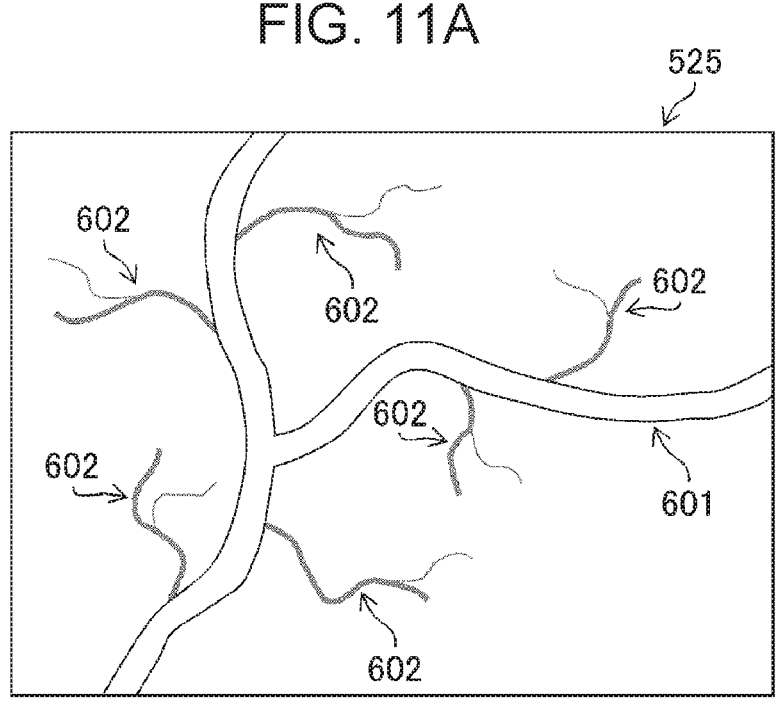
FIGS. 11A and 11B are diagrams illustrating an example of a first image and a second image.
Figure 11B:
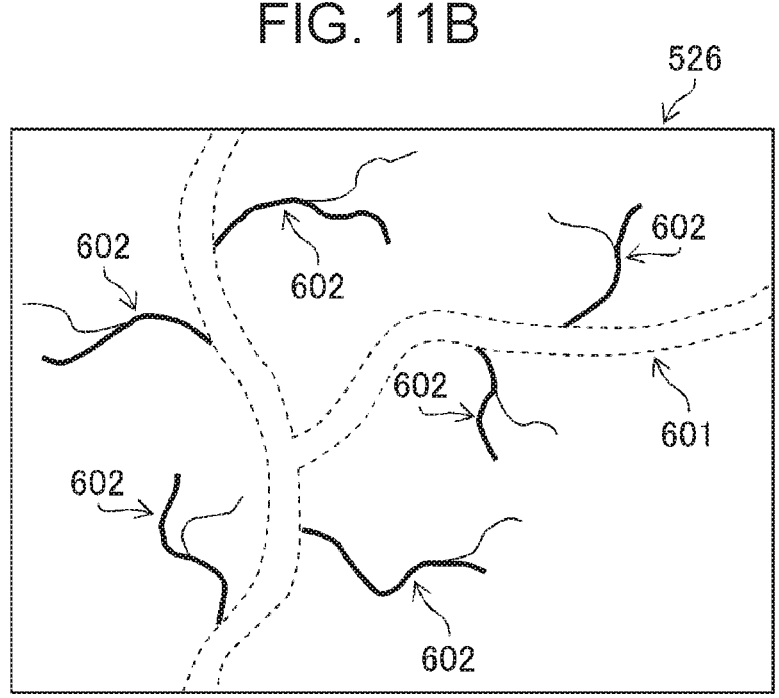

The first image and the second image are different in the wavelength of observation light as well as in imaging timing. Accordingly, in the first image (the image 525) using white light as observation light, thick blood vessels 601 are clearly seen but thin blood vessels 602 are not clearly seen as illustrated in FIG. 11A, for example. In contrast, in the second image (the image 526) using blue narrow-band light as observation light, the thick blood vessels 601 are not clearly seen but the thin blood vessels 602 are clearly seen as illustrated in FIG. 11B, for example, compared with the first image (the image 525). Thus, in the first embodiment, the image processing unit 204 (the image generating unit 204I) performs correction (preprocessing) for reducing the difference between the first image and the second image caused by the difference between the first observation light and the second observation light (step S200: an image correction step).

Figure 12:
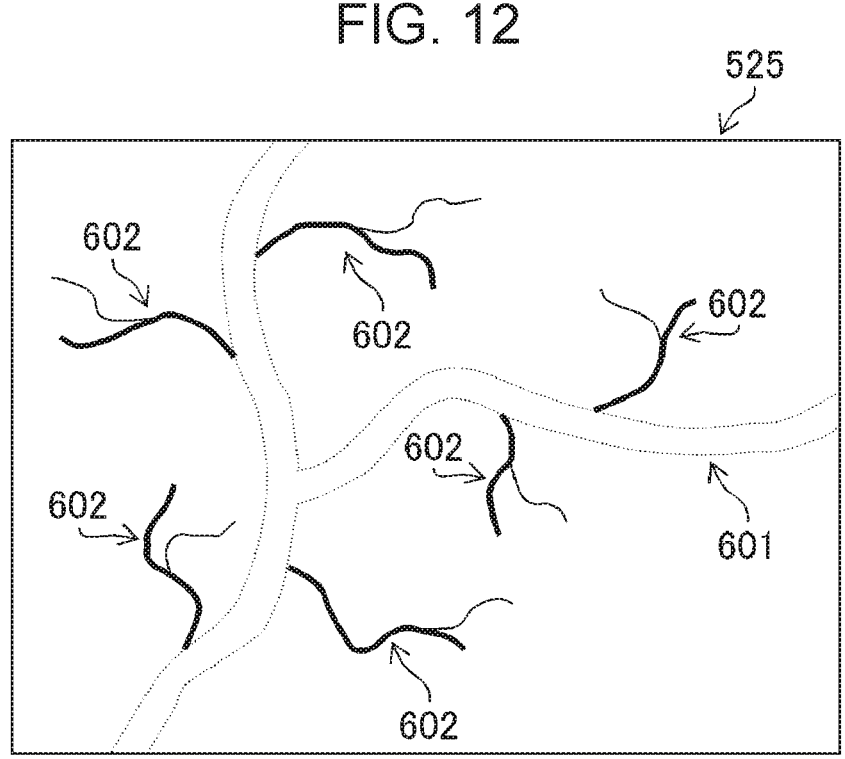
FIG. 12 is a diagram illustrating an example of a first image in which a common wavelength component is weighted.

Specifically, the image generating unit 204I extracts a wavelength component common to the first observation light and the second observation light in an image signal of the first image and an image signal of the second image, weights at least one of the image signal of the first image or the image signal of the second image with the extracted wavelength component, and generates an image in which the signal intensity of the common wavelength component is higher than the signal intensity of components other than the common wavelength component. In the first embodiment, the first observation light is white light and the second observation light is blue light, and thus the image generating unit 204I increases the weight of a blue light component which is a wavelength common to the image signal of the first image and the image signal of the second image. FIG. 12 illustrates an example of a state in which a blue light component is weighted in the image 525 (the first image), where the thin blood vessels 602 are relatively emphasized.

In the first embodiment, the alignment accuracy can be increased by such correction (preprocessing), and an image (an alignment first image) with a small change in the tint and structure of a photographic subject between frames can be acquired. Alternatively, an alignment first image may be generated by using only a common wavelength component instead of weighting the common wavelength component (a blue light component) as described above.

Calculation of Parameter and Alignment

Figure 13:
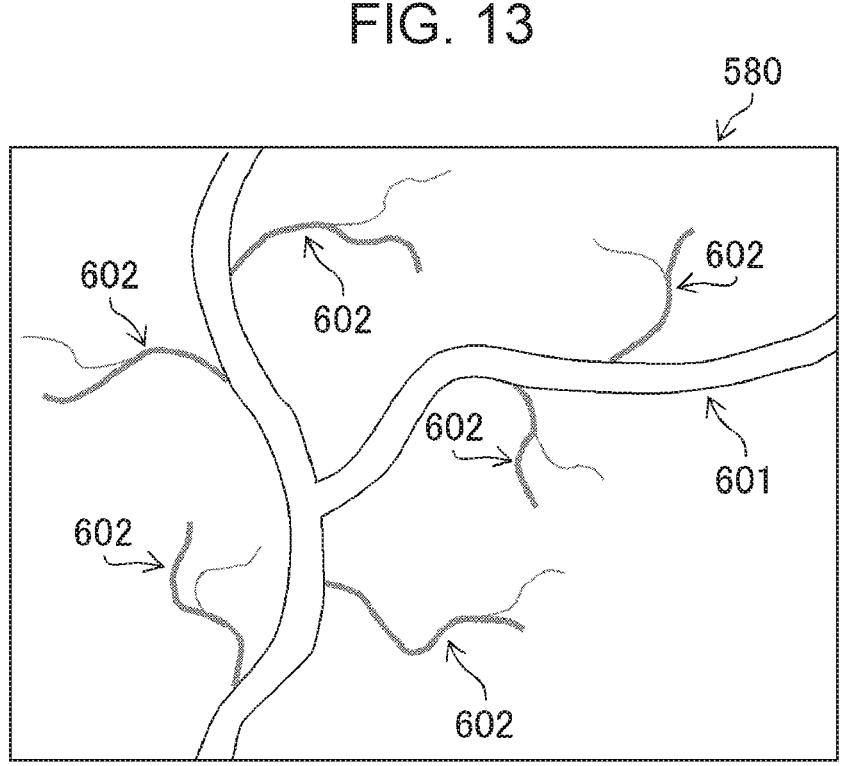
FIG. 13 is a diagram illustrating an example of an alignment first image.

The parameter calculating unit 204H calculates a parameter for achieving matching between the corrected (preprocessed) image 525 (the first image) and the image 526 (the second image) by alignment (step S202: a parameter calculation step). The parameter to be calculated is a parameter about at least one of relative movement, rotation, or deformation, and "deformation" may include enlargement or reduction. The image generating unit 204I applies the generated parameter to the corrected first image (the image 525) to generate an alignment first image (step S204: an image generation step). In steps S202 and S204, the parameter calculating unit 204H calculates a parameter for performing projective transformation between the first image and the second image, and the image generating unit 204I performs projective transformation based on the calculated parameter on the first image, and thereby being capable of generating an alignment first image. An example of the alignment first image (an image 580) is illustrated in FIG. 13. As described above, although the second image is used to calculate the parameter, the alignment first image is generated by moving or deforming the first image, and thus the tint of the alignment first image is not changed by an influence of pixel values of the second image.

Detection and Classification of Region of Interest

The region-of-interest detecting unit 204C detects a region of interest from the generated alignment first image (step S206: a region-of-interest detection step). The classifying unit 204D classifies the detected region of interest (step S208: a region-of-interest classification step). Detection and classification of the region of interest in the alignment first image can be performed similarly to the above-described steps S106, S112, and the like, and detection and classification may be performed together.

Output about Alignment First Image

The display control unit 204E, the region-of-interest detecting unit 204C, and the classifying unit 204D perform output about the alignment first image (step S210: a display control step, an output step). Output about the alignment first image can be performed, similarly to the above description about the first image, by displaying the alignment first image, information indicating a detection result of a region of interest, and information indicating a classification result of the region of interest on the monitor 400 by the display control unit 204E, the region-of-interest detecting unit 204C, and the classifying unit 204D (a display control step, an output step), and by recording these pieces of information in the recording unit 207 (an output step). Output about the alignment first image can be sequentially performed after output about the first image. For example, the display control unit 204E repeats display of M frames (in the case of the first image acquisition mode) or N frames (in the case of the second image acquisition mode) of the first image and display of one frame of the alignment first image (sequential display). Such sequential display may be performed in real time during a test of a photographic subject, or may be performed when a user views the first image and the alignment first image recorded in the recording unit 207 later. In a case where the alignment first image is generated by performing the above-described correction (weighting of a blue light component) on the first image, the image generating unit 204I may change the balance of wavelength components to the original balance so as be the same as white light when the alignment first image is output (displayed or the like). Accordingly, it is possible to prevent that an image of different wavelength balance is displayed on the monitor 400 and the user feels unnatural.

In this way, in the first embodiment, it is possible to display an alignment first image (step S124, S152) even at the timing when a first image is not acquired, in addition to display a normal first image (step S108, S138). Accordingly, a substantial decrease in the frame rate of the first image can be prevented, and the user is able to continue observation by using a normal-light image (a first image) captured by using normal light (white light).

Output about Region of Interest

In output (display, recording) about the first image and the alignment first image, in a case where a region of interest has been detected from the first image and/or the alignment first image, the display control unit 204E, the region-of-interest detecting unit 204C, and the classifying unit 204D are capable of outputting information indicating a detection result of the region of interest and/or information indicating a classification result of the region of interest. Output of the information can be performed by displaying information indicating the region of interest (for example, the position and size of the region of interest) and/or information indicating the classification result (for example, the type of the region of interest, classification of a polyp, diagnosis of the stage of cancer, or the like) on the monitor 400 by using characters, numerals, symbols, colors, and the like by the display control unit 204E, the region-of-interest detecting unit 204C, and the classifying unit 204D. These pieces of information may be displayed by superimposing them on the first image and/or the alignment first image.

Figure 14A:
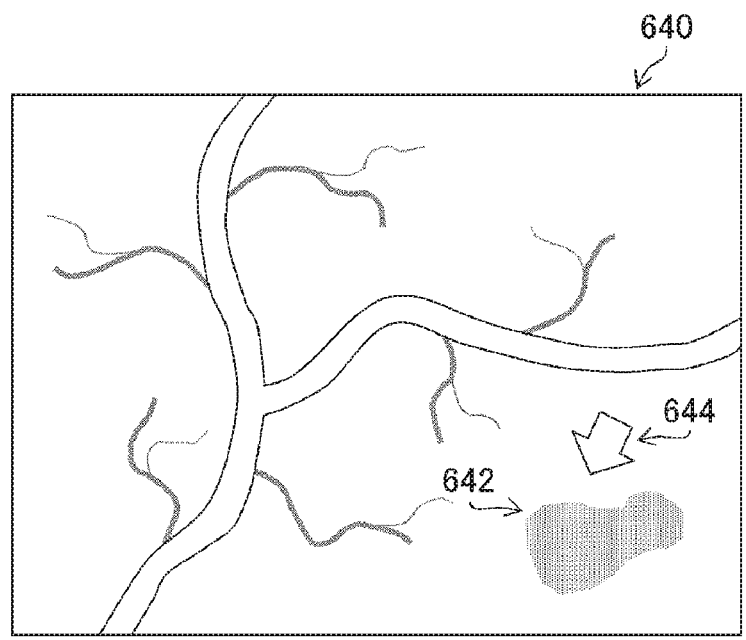
FIGS. 14A and 14B are diagrams illustrating display examples of information about a region of interest.
Figure 14B:
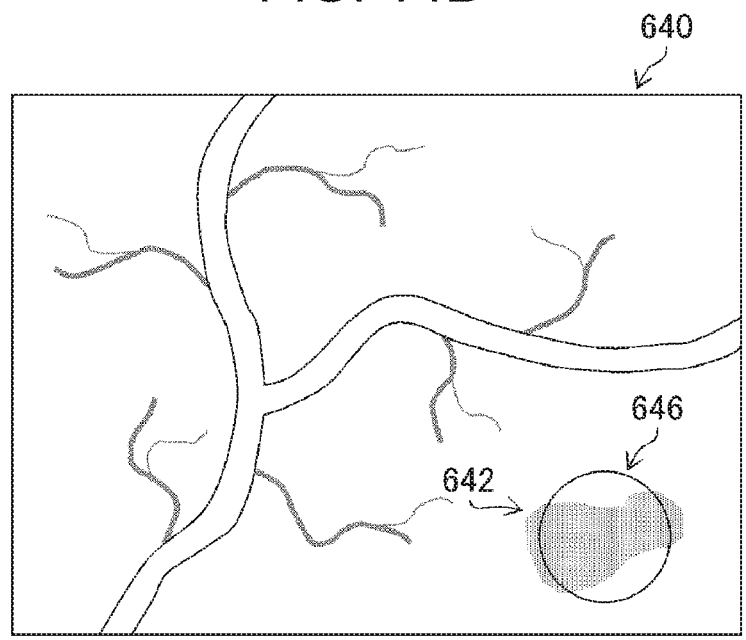

FIGS. 14A and 14B are diagrams illustrating display examples of information about a region of interest. FIG. 14A illustrates a state in which a symbol (an arrow 644) indicating the position of a region of interest 642 is displayed by superimposing it on an image 640. FIG. 14B illustrates a state in which a marker 646 (for example, a circle having a diameter of 5 mm) for measuring the size of the region of interest 642 is displayed by superimposing it on the image 640.

Example of Output about First Image and Second Image

In the first embodiment, the display control unit 204E, the region-of-interest detecting unit 204C, and the classifying unit 204D are capable of outputting (displaying, recording), regarding a second image, an image, a detection result of a region of interest, and a classification result of the region of interest (step S122, S150: a display control step, an output step), in addition to the above-described output about a first image and/or an alignment first image (step S108, S138, S210). As a result of output about the second image, the user is able to accurately detect and classify a region of interest or the like by using the second image (in the above-described example, an image obtained by using blue narrow-band light) while continuously observing the first image obtained by using normal light (white light). FIGS. 15A and 15B are diagrams illustrating a state in which an image 650 which is a first image (an alignment first image) and an image 660 which is a second image are displayed on the monitor 400. FIGS. 15A and 15B illustrate a state in which a region of interest 652 is detected and a marker 654 for measuring the size thereof is displayed.

In addition to or instead of such display on the monitor 400, the region-of-interest detecting unit 204C and the classifying unit 204D may output sound corresponding to information indicating a detection result and/or information indicating a classification result through the audio processing unit 209 and the speaker 209A. In addition, the region-of-interest detecting unit 204C and the classifying unit 204D may cause the recording unit 207 to record the information indicating a detection result and/or the information indicating a classification result.

After the processing for the alignment first image (step S200 to step S210) has finished, the processing proceeds to step S126, where whether or not a region of interest has been detected is determined in the above-described manner. In a case where the processing for the alignment first image is performed in step S152, the processing proceeds to step S154, where whether or not the first termination condition is satisfied is determined.

As described above, in the endoscope system 10 according to the first embodiment, a first image and a second image are acquired, in the first image acquisition mode in a case where a specific target (a region of interest) has not been detected, and in the second image acquisition mode until the first termination condition is satisfied in a case where a specific target has been detected. Accordingly, images (a first image and a second image) can be acquired in an appropriate imaging mode based on a detection result, and processing using the second image suitable for discrimination, classification, or the like can be performed when a region of interest is detected while observation with the first image is continued. In addition, in the case of acquiring images by using a plurality of types of observation light (first observation light and second observation light), generation and display of an alignment first image makes it possible to acquire an image with a small change in the tint and structure of a photographic subject between frames while preventing a substantial decrease in the frame rate of displaying an image (a first image), and accordingly an accurate structure of the photographic subject can be observed.

Processing in a Case where Specific Target is Agent and/or Equipment

Figure 16:
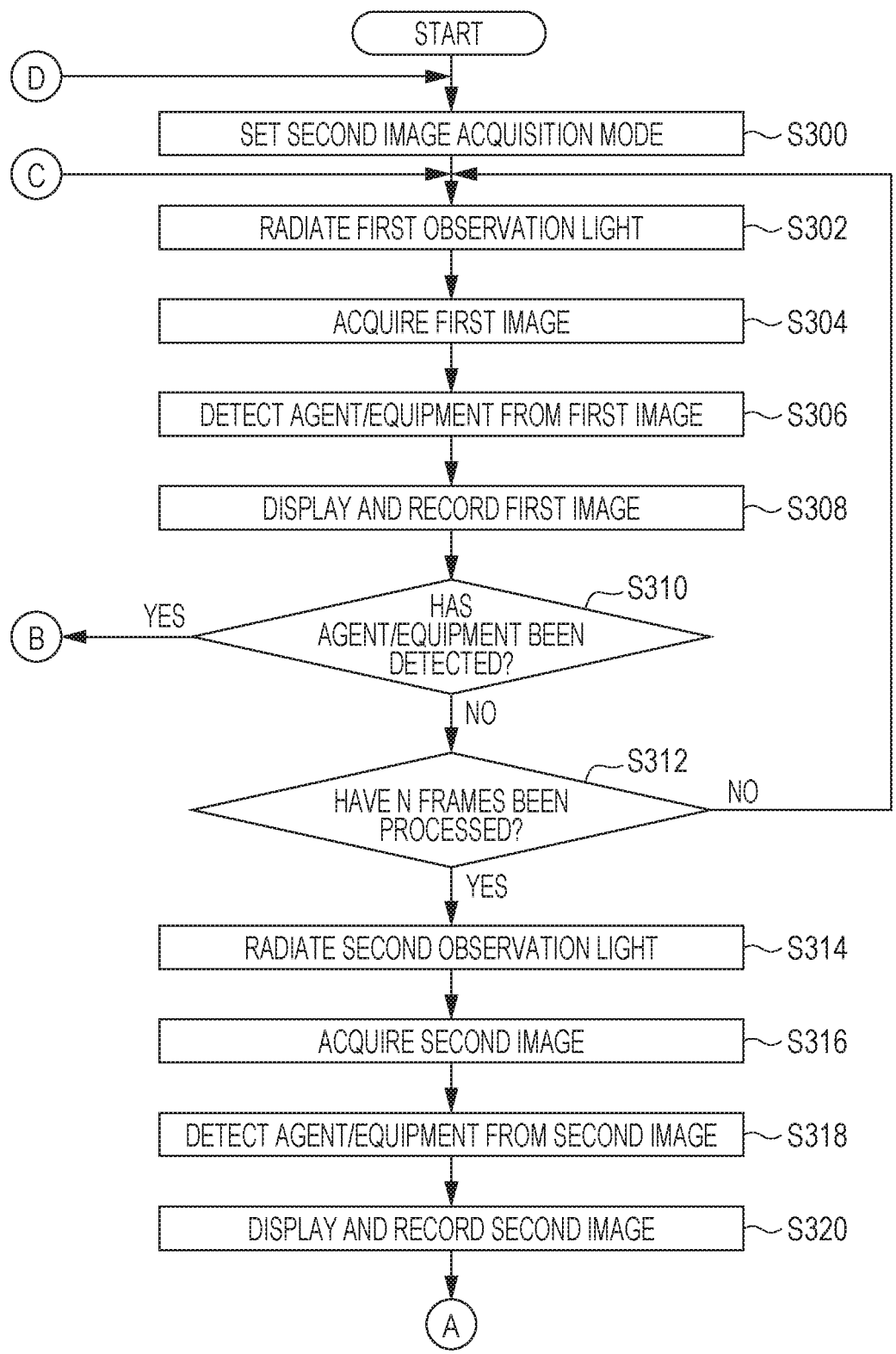
FIG. 16 is a flowchart illustrating processing in the case of detecting an agent and/or equipment.
Figure 17:
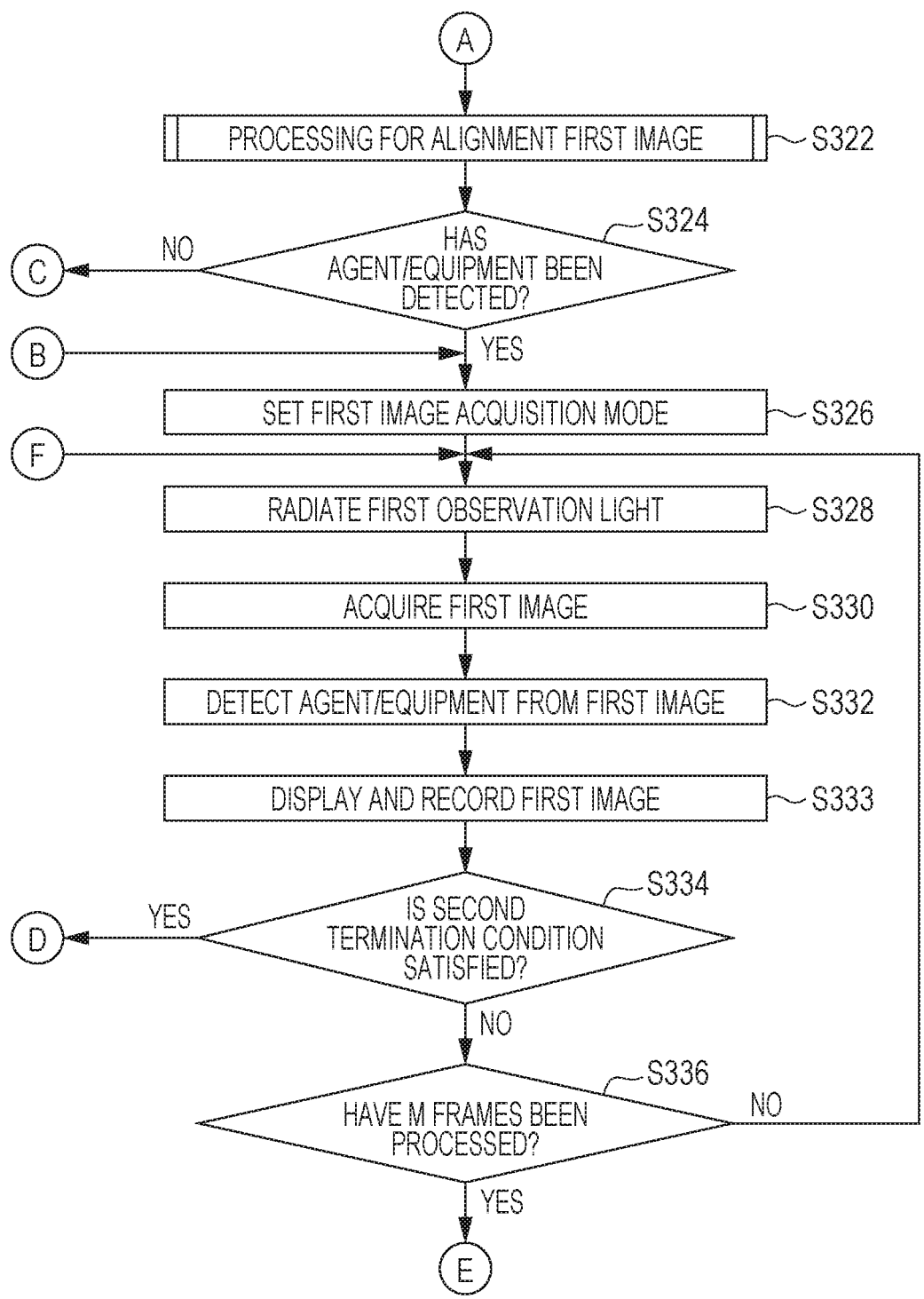
FIG. 17 is a flowchart (continued from FIG. 16) illustrating the processing in the case of detecting an agent and/or equipment.
Figure 18:
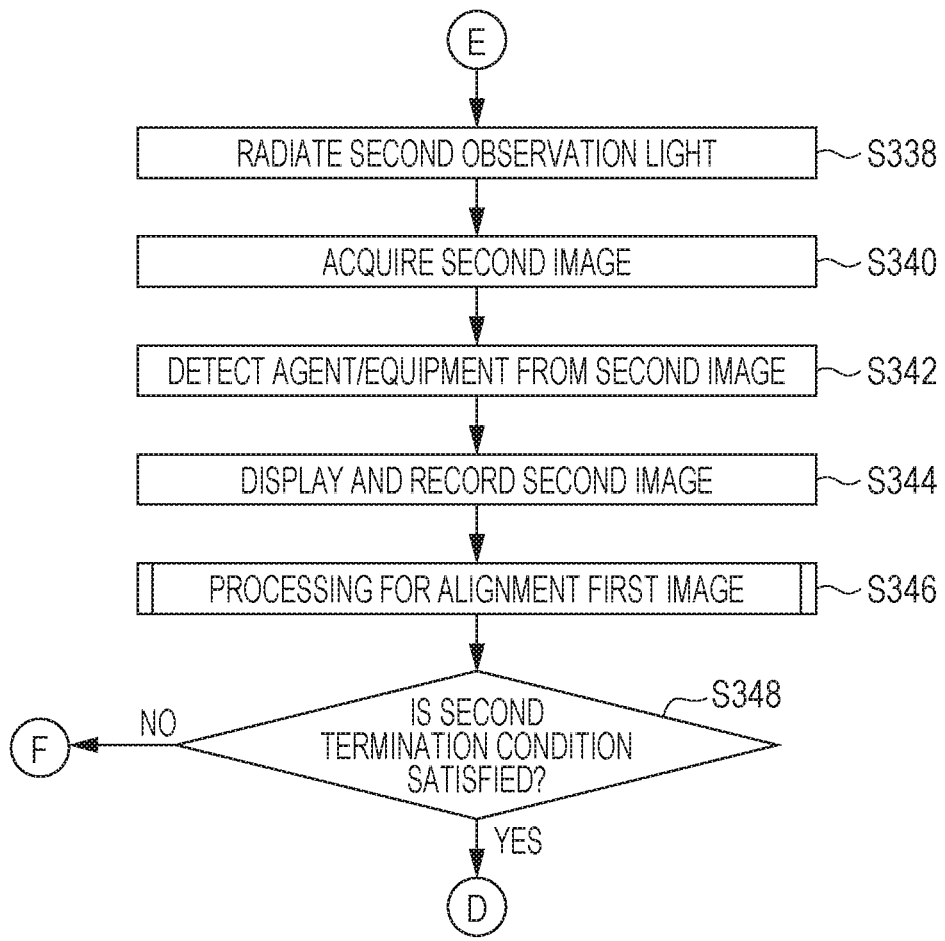
FIG. 18 is a flowchart (continued from FIG. 17) illustrating the processing in the case of detecting an agent and/or equipment.

FIGS. 16 to 18 are flowcharts illustrating processing in a case where a specific target is an agent and/or equipment. During treatment, a precise operation is often required and thus a decrease in the frame rate of displaying an image (displaying a first image) is not preferable. In addition, it is considered that, in the stage of performing treatment, a discrimination result of a lesion has been confirmed and thus necessity for automatic discrimination using a second image may be low. Thus, it is preferable to use the first image acquisition mode, in which the first image acquisition ratio is higher than in the second image acquisition mode, in a case where an agent and/or equipment used for treatment or the like has been detected. In a case where a pigment or a dye is applied to a lesion, a decrease in the frame rate of displaying an image (displaying a first image) is not preferable because the user is to carefully examine a minute structure of the lesion. Thus, it is preferable to use the first image acquisition mode, in which the first image acquisition ratio is higher than in the second image acquisition mode, in a case where an agent such as a pigment or a dye has been detected.

Also in this case, as in the above-described case of the processing for a region of interest, a description will be given of the case of acquiring, as a first image, a white-light image (a normal-light image) using white light as observation light (first observation light) and acquiring, as a second image, a blue-light image (a special-light image) using blue light which is narrow-band light (the center wavelength is shorter than that of the first observation light) as observation light (second observation light). However, the observation light and the images to be acquired are not limited to such a combination. As in the case of the processing for a region of interest, the second image may be a special-light image acquired by using, as observation light, green light, red light, infrared light, purple light, or the like which is narrow-band light. Alternatively, a first image and a second image may be acquired by using the first observation light and the second observation light each of which is narrow-band light (for example, first narrow-band light and second narrow-band light, such as blue light and green light, or red light beams having different wavelengths). Also in this case, it is assumed that a first image and a second image are captured by radiating only first observation light or second observation light in one frame.

In the flowchart in FIG. 16, in an initial state (a state in which an agent and/or equipment has not been detected), the mode control unit 204B sets the image acquiring unit 204A to the second image acquisition mode (step S300: a mode control step). A description of the case of setting the second image acquisition mode in the initial state is given because, if the first image acquisition mode is set in the initial state, the first image acquisition mode can be continued without switching the mode when an agent and/or equipment is detected.

Also in the case of detecting an agent and/or equipment, as in the case where a region of interest is a specific target, the first and second image acquisition modes can be set. Here, the image acquisition pattern in the first image acquisition mode is the pattern illustrated in FIG. 8A, and the image acquisition pattern in the second image acquisition mode is the pattern illustrated in FIG. 8B, but the image acquisition patterns are not limited to this example. For example, the pattern illustrated in FIG. 9 may be used in the first image acquisition mode, and the pattern illustrated in FIG. 8A may be used in the second image acquisition mode, or other patterns in which the second image acquisition ratios are different may be used.

The image acquiring unit 204A controls the light source control unit 350 to cause the red light source 310R, the green light source 310G, and the blue light source 310B to emit light and irradiate a subject with white light (first observation light) (step S302: an imaging step, an image acquisition step), and the imaging optical system 130, the imaging device 134, and so forth capture an image (a first image, a normal-light image) of the subject (step S304: an imaging step, an image acquisition step). The captured image is acquired by (input to) the image acquiring unit 204A via the image input controller 202 (step S304: an image acquisition step).

Method for Detecting Agent

The detector 204F (a specific target detecting unit, a detector) detects an agent and/or equipment as a specific target from the acquired first image (step S306: a specific target detection step, a detection step). Detection of an agent (including a pigment or a dye) in step S306 can be performed on the basis of a color tone feature quantity by using, for example, the method described in the above-mentioned JP2016-62488A. Specifically, the image processing unit 204 (the detector 204F) excludes dark pixels and halation pixels on the basis of red (R), green (G), and blue (B) pixel values of the individual pixels of a medical image, calculates a color tone feature quantity (G/R, B/G) of each pixel that has not been excluded, and calculates an average value of the color tone feature quantity in each of small blocks obtained by dividing the medical image. An average value of G/R is represented by μGR, an average value of B/G is represented by μBG, and μGR and μBG are plotted. The plotting result indicates different distributions according to individual agents (pigments, dyes, or the like). Thus, as a result of comparing the plotting result (the position in a feature quantity space) of the detected target agent with distributions of individual agents, the agent used in the acquired medical image can be determined. A detection result (for example, the type or name of an agent) may be associated in advance with the details of treatment or technique performed by using the type, and may be included in detection information given to the image.

Detection of an agent may be performed by using a deep learning algorithm, as in the above description of "detection of region of interest based on deep learning algorithm".

Method for Detecting Equipment

Detection of equipment in step S306 can be performed by using the method described in the above-mentioned JP2016-62488A. Specifically, endoscopic images of individual treatment tools each inserted through a forceps channel (a pipe line communicating with the forceps port 126, which is not illustrated) are used as template images, and the detector 204F compares the template images with an endoscopic image obtained during a test, thereby detecting that any treatment tool has been used. As the template image of each treatment tool, a plurality of images are prepared in which the direction of the forceps channel, the length of protrusion, and the open/closed state are different. In addition, a plurality of images of different rotation angles are prepared for an asymmetrical treatment tool whose shape on an image is changed by rotation.

To detect a treatment tool from an endoscopic image, the detector 204F detects an edge from the endoscopic image (here, a first image). As an image for edge detection, an R image (an image generated from pixel signals of red pixels) or a G image (an image generated from pixel signals of green pixels) is used. In a case where a treatment tool sheath is red, a G image may be used. A line shape is detected from the edge image by using template matching, Hough transformation, or the like, the detected line shape is compared with template images, and the degrees of match are calculated. The treatment tool in the template image having the highest degree of match is regarded as a detection result. A detection result (for example, the type or name of equipment) may be associated in advance with the details of treatment or technique performed by using the equipment, and may be included in detection information given to the image.

Detection of equipment may be performed by using a deep learning algorithm, as in detection of an agent.

Display and Recording of First Image

The detector 204F and the display control unit 204E perform output (display, recording) about a white-light image (a first image) (step S308: a display control step, an output step). As in the case of a region of interest, the output can be performed by displaying a white-light image (a first image), information indicating a detection result, and so forth on the monitor 400 (a display control step) and by recording the information in the recording unit 207 (an output step), outputting sound from the speaker 209A, or the like. In addition, while a first image (and an alignment first image) is continuously recorded as a moving image, a frame in which an agent and/or equipment has been detected may be recorded as a still image.

The detector 204F determines whether or not an agent and/or equipment has been detected from the acquired first image (step S310). If the determination is affirmative, the processing proceeds to step S326. In this case, the mode control unit 204B causes the image acquiring unit 204A to acquire a first image and a second image in the first image acquisition mode until the second termination condition is satisfied (step S328 to step S348). On the other hand, if the determination in step S310 is negative, processing on the first image is repeated for N frames (N is an integer; 2 in the case of the pattern in FIG. 8B) (while the determination in step S312 is NO). After this step ends (YES in step S312), the processing proceeds to step S314.

In step S314, the image acquiring unit 204A controls the light source control unit 350 to cause the blue light source 310B to emit light and irradiate a subject with blue narrow-band light (special light, second observation light) (an imaging step, an image acquisition step), and the imaging optical system 130, the imaging device 134, and so forth capture (acquire) an image (a second image, a special-light image) of the subject (step S316: an imaging step, an image acquisition step). The processing of detecting an agent and/or equipment on the acquired second image (step S318), output (display, recording) processing (step S320), and the like can be performed similarly to that for the first image. The processing for an alignment first image (step S322 in FIG. 17) can also be performed similarly to the above-described step S124. Accordingly, a substantial decrease in the frame rate of the first image can be prevented, and the user is able to continue observation by using a normal-light image (a first image) captured by using normal light (white light).

The detector 204F determines whether or not an agent and/or equipment has been detected from the acquired second image (step S324). If the determination is affirmative, the processing proceeds to step S326, where acquisition of images is performed in the first image acquisition mode. On the other hand, if the determination in step S324 is negative, the processing returns to step S302, where acquisition of images (a first image and a second image) is continued in the second image acquisition mode.

In step S326, the mode control unit 204B sets the image acquiring unit 204A to the first image acquisition mode, causes the image acquiring unit 204A to acquire a first image and a second image in the first image acquisition mode until the second termination condition is satisfied (YES in step S334 or step S348), and performs processing of detecting an agent and/or equipment on the acquired images (step S328 to step S348). The acquisition of the first image and the second image and the processing on these images (step S328 to step S348) are the same as the description given above about step S302 to step S324 except that the second image acquisition ratio is different, and thus the detailed description thereof is omitted. Here, the pattern illustrated in FIG. 8A is used in the first image acquisition mode, and the pattern illustrated in FIG. 8B is used in the second image acquisition mode. In this case, the second image acquisition ratio in the first image acquisition mode (the first ratio) is not zero, and thus a second image is acquired in the first image acquisition mode. However, in a case where the second image acquisition ratio is zero in the first image acquisition mode (in a case where the pattern illustrated in FIG. 9 is used in the first image acquisition mode), the processing from step S336 to step S346 is not performed.

As the "second termination condition" in steps S334 and S348, for example, the elapse of a predetermined time, no more detection of an agent and/or equipment, acquisition of a predetermined number of still images, a termination instruction from a user, or the like can be used, but the condition is not limited to these examples. If the second termination condition is satisfied in step S334 or step S348 (FIG. 18), the processing returns to step S300, where the mode control unit 204B causes the image acquiring unit 204A to acquire a first image and a second image in the second image acquisition mode (step S302 to step S324).

As described above, in the endoscope system 10, in a case where an agent and/or equipment has been detected as a specific target, a first image and a second image are acquired in the first image acquisition mode until the second termination condition is satisfied. Accordingly, images (a first image and a second image) can be acquired in an appropriate imaging mode based on a detection result, and when a region of interest is detected, acquisition and display of an image can be performed in the first image acquisition mode, which is suitable for precise operation, observation of a minute structure, and the like. In addition, in the first image acquisition mode, the first image acquisition ratio is higher than in the second image acquisition mode and thus a decrease in the frame rate of displaying an image (a first image) can be prevented. In addition, in the case of acquiring images by using a plurality of types of observation light (first observation light and second observation light), an image with a small change in the tint and structure of a photographic subject between frames can be acquired while preventing a substantial decrease in the frame rate of displaying an image (a first image) by generating and displaying an alignment first image. Accordingly, an accurate structure of the photographic subject can be observed.

Other Configurations of Light Source and Effect of Applying the Present Invention A description will be given of examples of another configuration of a light source in the endoscope system according to the present invention and an effect of applying the present invention in that case.

Example 1

Figure 19:
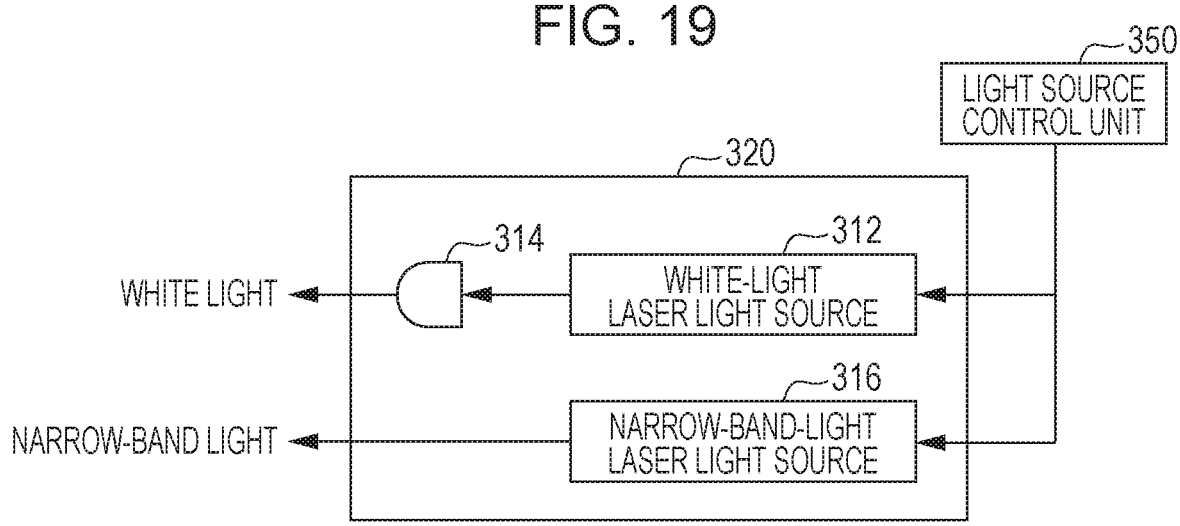
FIG. 19 is a diagram illustrating an example of the configuration of a light source.

As illustrated in FIG. 19, a light source apparatus 320 (a light source apparatus) includes a white-light laser light source 312 (a white-light laser light source) that radiates white-light laser as excitation light, a fluorescent body 314 (a fluorescent body) that emits white light as first observation light when irradiated with white-light laser, and a narrow-band-light laser light source 316 (a narrow-band-light laser light source) that radiates narrow-band light as second observation light (for example, blue narrow-band light, or green narrow-band light or red narrow-band light). The light source apparatus 320 is controlled by the light source control unit 350. In FIG. 19, illustration of the components of the endoscope system 10 is omitted, except for the light source apparatus 320 and the light source control unit 350. In the case of using the white-light laser light source 312 to acquire white light as first observation light, if the second image acquisition ratio is high (for example, in the case of the above-described pattern illustrated in FIG. 8C), repetition of radiation and non-radiation of first observation light increases. Thus, repetition of excitation and non-excitation of the white-light laser light source 312 increases, which may hasten degradation of the light source.

However, since the endoscope system 10 includes the image processing apparatus according to the present invention, an advantageous effect of including the image processing apparatus is acquired. That is, it is possible to prevent that the second image acquisition mode is set and the second image acquisition ratio increases even in a case where the necessity for a second image is low (for example, a case were a region of interest is not detected as a specific target or a case where an agent and/or equipment is detected as a specific target) and increased repetition of radiation and non-radiation of first observation light unnecessarily hastens degradation of the light source.

Example 2

Figure 20:
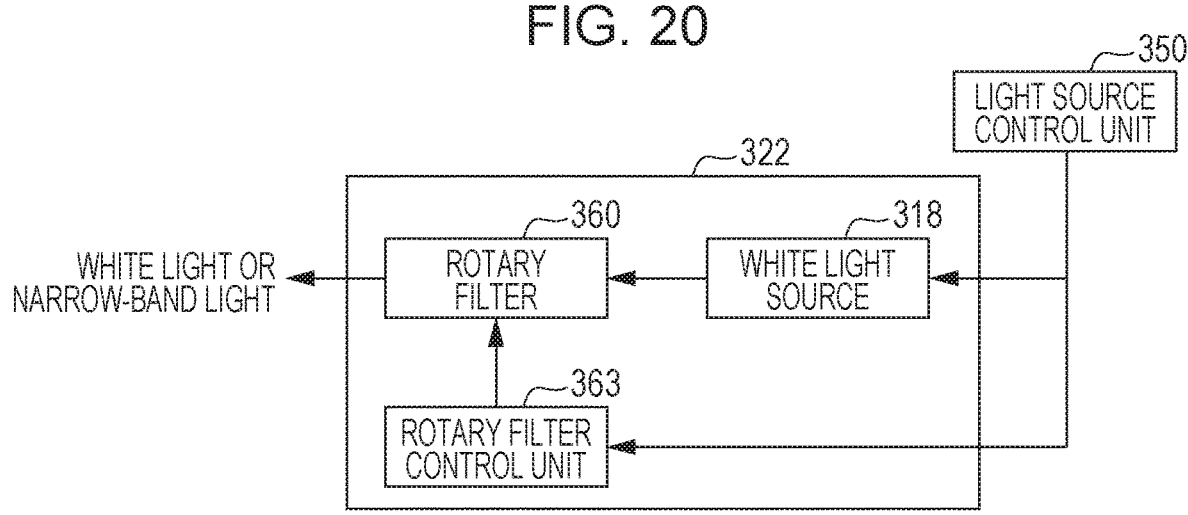
FIG. 20 is a diagram illustrating another example of the configuration of a light source.

As illustrated in FIG. 20, a light source apparatus 322 (a light source apparatus) includes a white light source 318 (a white light source) that emits white light, a rotary filter 360 (a white-light filter, a narrow-band-light filter) in which a white-light region that allows white light to pass therethrough and a narrow-band-light region that allows narrow-band light to pass therethrough are formed, and a rotary filter control unit 363 (a first filter switching control unit) that controls rotation of the rotary filter 360 to insert the white-light region or the narrow-band-light region to the optical path of white light. The white light source 318 and the rotary filter control unit 363 are controlled by the light source control unit 350. In FIG. 20, illustration of the components of the endoscope system 10 is omitted, except for the light source apparatus 322 and the light source control unit 350. In the case of generating a plurality of types of observation light (for example, white light as first observation light and narrow-band light as second observation light) by controlling the rotation of the rotary filter 360, lack of synchronization between the rotation of the rotary filter 360 and the read-out timing of the image sensor (the imaging device 134) may cause an imbalance in the color of a first image and/or a second image. However, since the endoscope system 10 includes the image processing apparatus according to the present invention, an advantageous effect of including the image processing apparatus is acquired. That is, it is possible to reduce the possibility that the second image acquisition mode is set and the number of times of switching of the light source or the filter increases even in a case where the necessity for a second image is low (for example, a case were a region of interest is not detected as a specific target or a case where an agent and/or equipment is detected as a specific target), and the color balance of a first image and/or a second image is lost.

In example 2, the white light source 318 may use a white light source that emits wide-band light, or may generate white light by causing light sources that emit red light, blue light, and green light to simultaneously radiate light. In addition, the rotary filter 360 and the rotary filter control unit 363 may be provided in the light source 310 illustrated in FIG. 2.

Figure 21A:
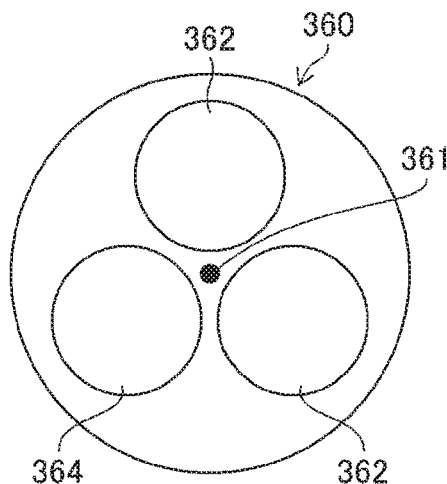
FIGS. 21A and 21B are diagrams illustrating examples of a rotary filter.
Figure 21B:
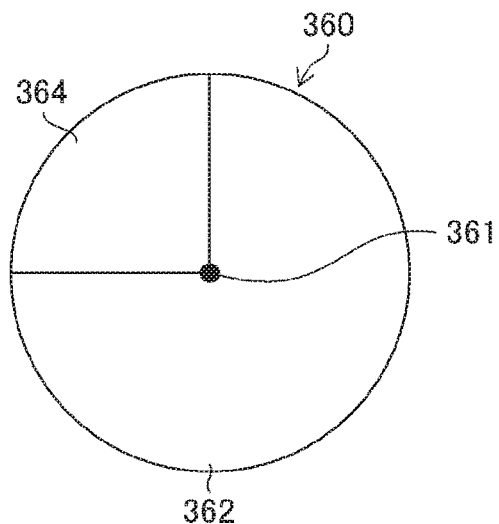

FIGS. 21A and 21B are diagrams illustrating examples of the rotary filter 360. In the example illustrated in FIG. 21A, two circular white-light regions 362 (white-light filters) that allow white light to pass therethrough and one circular narrow-band-light region 364 (a narrow-band-light filter) that allows narrow-band light to pass therethrough are formed in the rotary filter 360. By rotating the rotary filter 360 around a rotational axis 361 under control by the rotary filter control unit 363 (a first filter switching control unit), the white-light region 362 or the narrow-band-light region 364 is inserted to the optical path of white light, and accordingly a subject is irradiated with white light or narrow-band light. The narrow-band-light region 364 can be a region that allows any narrow-band light, such as red narrow-band light, blue narrow-band light, green narrow-band light, or purple narrow-band light, to pass therethrough. The number and arrangement of white-light regions 362 and narrow-band-light regions 364 are not limited to the example illustrated in FIG. 21A and may be changed in accordance with the radiation ratio of white light and narrow-band light.

The shapes of the white-light region and the narrow-band-light region are not limited to circular as illustrated in FIG. 21A and may be a fan-shape as illustrated in FIG. 21B. FIG. 21B illustrates an example in which ¾ of the rotary filter 360 is used as the white-light region 362 and ¼ of the rotary filter 360 is used as the narrow-band-light region 364. The area of the fan-shape can be changed in accordance with the radiation ratio of white light and narrow-band light. In the examples in FIGS. 21A and 21B, a plurality of narrow-band-light regions corresponding to different types of narrow-band light may be provided in the rotary filter 360.

Figure 22A:
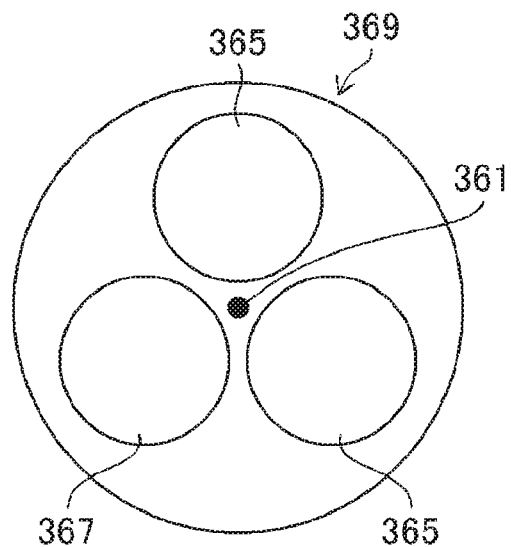
FIGS. 22A and 22B are diagrams illustrating other examples of a rotary filter.
Figure 22B:
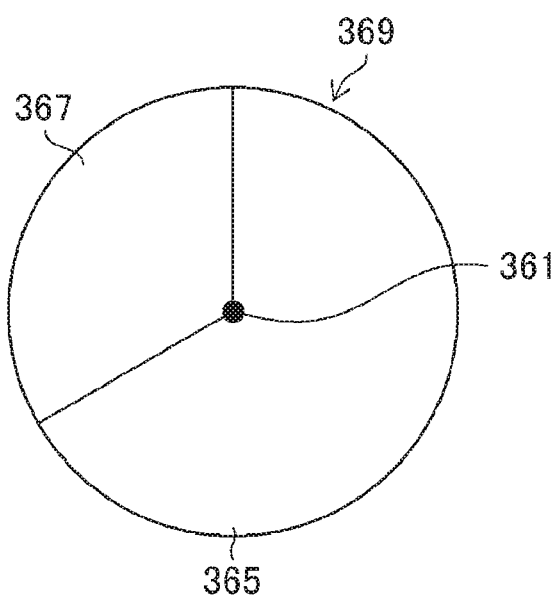

FIGS. 22A and 22B are diagrams illustrating other examples of the rotary filter. As a white light source for the rotary filters illustrated in FIGS. 22A and 22B, the white light source 318 can be used as in the light source apparatus 322 illustrated in FIG. 20. A rotary filter 369 illustrated in FIG. 22A is not provided with a white-light region that allows white light to pass therethrough, unlike the rotary filter 360 illustrated in FIGS. 20, 21A, and 21B, but is provided with two circular first-narrow-band-light regions 365 (first-narrow-band-light filters) that allow a component of first narrow-band light in white light to pass therethrough and one circular second-narrow-band-light region 367 (a second-narrow-band-light filter) that allows a component of second narrow-band light in white light to pass therethrough. By rotating the rotary filter 369 around the rotational axis 361 under control by the rotary filter control unit 363 (see FIG. 20; a second filter switching control unit), the first-narrow-band-light region 365 (a first-narrow-band-light filter) or the second-narrow-band-light region 367 (a second-narrow-band-light filter) is inserted to the optical path of white light emitted by the white light source 318, and accordingly a subject can be irradiated with first narrow-band light or second narrow-band light.

The shapes of the first-narrow-band-light regions 365 and the second-narrow-band-light region 367 are not limited to circular as illustrated in FIG. 22A and may be a fan-shape as illustrated in FIG. 22B. FIG. 22B illustrates an example in which ⅔ of the rotary filter 369 is used as the first-narrow-band-light region 365 and ⅓ of the rotary filter 369 is used as the second-narrow-band-light region 367. The area of the fan-shape can be changed in accordance with the radiation ratio of first narrow-band light and second narrow-band light. In the examples in FIGS. 22A and 22B, three or more narrow-band-light regions corresponding to different types of narrow-band light may be provided in the rotary filter 369.

In the case of generating a plurality of types of observation light (first narrow-band light and second narrow-band light) by switching the filter by the rotary filter control unit 363, lack of synchronization between switching of the filter and the read-out timing of the image sensor (the imaging device 134) may cause an imbalance in the color of a first image and/or a second image. However, since the endoscope system 10 includes the image processing apparatus according to the present invention, an advantageous effect of including the image processing apparatus is acquired. That is, it is possible to reduce the possibility that the second image acquisition mode is set and the number of times of switching of the light source or the filter increases even in a case where the necessity for a second image is low (for example, a case were a region of interest is not detected as a specific target or a case where an agent and/or equipment is detected as a specific target), and the color balance of a first image and/or a second image is lost.

Appendices

In addition to the individual aspects of the above-described embodiment, the configurations described below are included in the scope of the present invention.

Appendix 1

A medical image processing apparatus wherein
a medical image analysis processing unit detects a region of interest on the basis of a feature quantity of pixels of a medical image, the region of interest being a region to be focused on, and
a medical image analysis result acquiring unit acquires an analysis result of the medical image analysis processing unit.

Appendix 2

A medical image processing apparatus wherein
a medical image analysis processing unit detects presence or absence of a target to be focused on the basis of a feature quantity of pixels of a medical image, and
a medical image analysis result acquiring unit acquires an analysis result of the medical image analysis processing unit.

Appendix 3

The medical image processing apparatus wherein
the medical image analysis result acquiring unit acquires the analysis result of the medical image from a recording device in which the analysis result is recorded, and
the analysis result is either or both of the region of interest which is a region to be focused on included in the medical image and the presence or absence of the target to be focused on.

Appendix 4

The medical image processing apparatus wherein the medical image is a normal-light image acquired by radiating light in a white range or light in a plurality of wavelength ranges as the light in the white range.

Appendix 5

The medical image processing apparatus wherein
the medical image is an image acquired by radiating light in a specific wavelength range, and
the specific wavelength range is a range narrower than a white wavelength range.

Appendix 6

The medical image processing apparatus wherein the specific wavelength range is a blue or green range in a visible range.

Appendix 7

The medical image processing apparatus wherein the specific wavelength range includes a wavelength range of 390 nm or more and 450 nm or less or a wavelength range of 530 nm or more and 550 nm or less, and the light in the specific wavelength range has a peak wavelength in the wavelength range of 390 nm or more and 450 nm or less or the wavelength range of 530 nm or more and 550 nm or less.

Appendix 8

The medical image processing apparatus wherein the specific wavelength range is a red range in a visible range.

Appendix 9

The medical image processing apparatus wherein the specific wavelength range includes a wavelength range of 585 nm or more and 615 nm or less or a wavelength range of 610 nm or more and 730 nm or less, and the light in the specific wavelength range has a peak wavelength in the wavelength range of 585 nm or more and 615 nm or less or the wavelength range of 610 nm or more and 730 nm or less.

Appendix 10

The medical image processing apparatus wherein the specific wavelength range includes a wavelength range in which a light absorption coefficient is different between oxyhemoglobin and deoxyhemoglobin, and the light in the specific wavelength range has a peak wavelength in the wavelength range in which the light absorption coefficient is different between oxyhemoglobin and deoxyhemoglobin.

Appendix 11

The medical image processing apparatus wherein the specific wavelength range includes a wavelength range of 400±10 nm, a wavelength range of 440±10 nm, a wavelength range of 470±10 nm, or a wavelength range of 600 nm or more and 750 nm or less, and the light in the specific wavelength range has a peak wavelength in the wavelength range of 400±10 nm, the wavelength range of 440±10 nm, the wavelength range of 470±10 nm, or the wavelength range of 600 nm or more and 750 nm or less.

Appendix 12

The medical image processing apparatus wherein
the medical image is an inside-of-living-body image depicting an inside of a living body, and
the inside-of-living-body image has information about fluorescence emitted by a fluorescent substance in the living body.

Appendix 13

The medical image processing apparatus wherein the fluorescence is acquired by irradiating the inside of the living body with excitation light whose peak is 390 nm or more and 470 nm or less.

Appendix 14

The medical image processing apparatus wherein
the medical image is an inside-of-living-body image depicting an inside of a living body, and
the specific wavelength range is a wavelength range of infrared light.

Appendix 15

The medical image processing apparatus wherein the specific wavelength range includes a wavelength range of 790 nm or more and 820 nm or less or a wavelength range of 905 nm or more and 970 nm or less, and the light in the specific wavelength range has a peak wavelength in the wavelength range of 790 nm or more and 820 nm or less or the wavelength range of 905 nm or more and 970 nm or less.

Appendix 16

The medical image processing apparatus wherein
a medical image acquiring unit includes a special-light image acquiring unit that acquires a special-light image having information about the specific wavelength range on the basis of a normal-light image that is acquired by radiating light in a white range or light in a plurality of wavelength ranges as the light in the white range, and
the medical image is the special-light image.

Appendix 17

The medical image processing apparatus wherein a signal in the specific wavelength range is acquired through computation based on color information of RGB or CMY included in the normal-light image.

Appendix 18

The medical image processing apparatus including
a feature quantity image generating unit that generates a feature quantity image through computation based on at least one of a normal-light image or a special-light image, the normal-light image being acquired by radiating light in a white range or light in a plurality of wavelength ranges as the light in the white range, the special-light image being acquired by radiating light in a specific wavelength range, wherein
the medical image is the feature quantity image.

Appendix 19

An endoscope apparatus including:
the medical image processing apparatus according to any one of appendices 1 to 18; and
an endoscope that acquires an image by radiating at least any one of light in a white wavelength range or light in a specific wavelength range.

Appendix 20

A diagnosis assistance apparatus including the medical image processing apparatus according to any one of appendices 1 to 18.

Appendix 21

A medical work assistance apparatus including the medical image processing apparatus according to any one of appendices 1 to 18.

The embodiment of the present invention and other aspects have been described above. The present invention is not limited to the above-described aspects and various modifications can be made without deviating from the spirit of the present invention.

REFERENCE SIGNS LIST 10 endoscope system
100 endoscope main body
102 handheld operation section
104 insertion section
106 universal cable
108 light guide connector
112 soft part
114 bending part
116 tip rigid part
116A distal-end-side surface
123 illumination unit
123A illumination lens
123B illumination lens
126 forceps port
130 imaging optical system
132 imaging lens
134 imaging device
136 driving circuit
138 AFE
141 air/water supply button
142 suction button
143 function button
144 imaging button
170 light guide
200 processor
202 image input controller
204 image processing unit
204A image acquiring unit
204B mode control unit
204C region-of-interest detecting unit
204D classifying unit
204E display control unit
204F detector
204G ratio setting unit
204H parameter calculating unit
204I image generating unit
205 communication control unit 206 video output unit
207 recording unit
208 operation unit
209 audio processing unit
209A speaker
210 CPU
211 ROM
212 RAM
300 light source apparatus
310 light source
310B blue light source
310G green light source
310R red light source
312 white-light laser light source
314 fluorescent body
316 narrow-band-light laser light source
318 white light source
320 light source apparatus
322 light source apparatus
330 diaphragm
340 condenser lens
350 light source control unit
360 rotary filter
361 rotational axis
362 white-light region
363 rotary filter control unit
364 narrow-band-light region
365 first-narrow-band-light region
367 second-narrow-band-light region
369 rotary filter
400 monitor
501 image
502 image
503 image
504 image
505 image
506 image
507 image
508 image
509 image
510 image
511 image
512 image
521 image
522 image
523 image
524 image
525 image
526 image
527 image
532 image
541 image
542 image
543 image
544 image
545 image
546 image
547 image
548 image
549 image
550 image
551 image
552 image
561 image
562 image
563 image
564 image
565 image
566 image
567 image
568 image
569 image
570 image
571 image
572 image
601 blood vessel
602 blood vessel
640 image
642 region of interest
644 arrow
646 marker
650 image
652 region of interest
654 marker
660 image
S100 to S348 individual steps of image processing method
t time axis
T time range

What is claimed is:

1. An image processing apparatus comprising:
an image acquiring unit that acquires a first image and a second image that are captured at different times, the image acquiring unit acquiring the first image that is captured by using a first observation light and the second image that is captured by using a second observation light different from the first observation light;
a mode control unit that causes the image acquiring unit to acquire the first image and the second image in either a first image acquisition mode of acquiring the first image and the second image such that a ratio of the number of acquired frames of the second image to the number of acquired frames of the first image in a predetermined time range is a first ratio, or a second image acquisition mode of acquiring the first image and the second image such that a ratio of the number of acquired frames of the second image to the number of acquired frames of the first image in the time range is a second ratio higher than the first ratio;
a specific target detecting unit that detects a specific target from the first image and/or the second image; and
a display control unit that causes a display apparatus to display the first image, wherein
the mode control unit causes the image acquiring unit to acquire the first image and the second image in the first image acquisition mode or the second image acquisition mode on the basis of a detection result of the specific target,
when the specific target detecting unit has detected the region of interest, the mode control unit causes the image acquiring unit to acquire the first image and the second image in the second image acquisition mode until a first termination condition is satisfied, and
wherein a light source apparatus irradiates a subject with the first observation light, the first observation light being white light including light in a red wavelength range, a blue wavelength range, and a green wavelength range, and irradiates the subject with the second observation light, the second observation light being narrow-band light corresponding to any one of the red wavelength range, the blue wavelength range, and the green wavelength range.

2. The image processing apparatus according to claim 1, wherein
the specific target detecting unit is a region-of-interest detecting unit that detects a region of interest,
in a case where the region-of-interest detecting unit has not detected the region of interest, the mode control unit causes the image acquiring unit to acquire the first image and the second image in the first image acquisition mode.

3. The image processing apparatus according to claim 2, wherein in a case where the first termination condition is satisfied, the mode control unit causes the image acquiring unit to acquire the first image and the second image in the first image acquisition mode.

4. The image processing apparatus according to claim 2, further comprising a classifying unit that performs classification of the region of interest on the basis of at least one of the first image and the second image.

5. The image processing apparatus according to claim 4, wherein the display control unit causes the display apparatus to display information indicating a result of the classification.

6. The image processing apparatus according to claim 1, wherein
the specific target detecting unit is a detector that detects an agent and/or equipment used for a subject, and
in a case where the detector has detected the agent and/or the equipment, the mode control unit causes the image acquiring unit to acquire the first image and the second image in the first image acquisition mode until a second termination condition is satisfied.

7. The image processing apparatus according to claim 1, wherein the mode control unit has a ratio setting unit that sets the first ratio and/or the second ratio.

8. The image processing apparatus according to claim 7, wherein the ratio setting unit sets the first ratio to zero and sets the second ratio to a value greater than zero.

9. The image processing apparatus according to claim 1, further comprising:
a parameter calculating unit that calculates a parameter for aligning the first image and the second image; and
an image generating unit that generates an alignment first image by applying the parameter to the first image, wherein
the display control unit causes the display apparatus to display the aligned first image at a timing when the second image is acquired.

10. The image processing apparatus according to claim 9, wherein the parameter calculating unit calculates the parameter for aligning the second image and the first image, the first image being captured at an imaging time that is before an imaging time of the second image and that has a temporal difference smaller than or equal to a threshold value from the imaging time of the second image.

11. The image processing apparatus according to claim 1, wherein the image acquiring unit acquires, as the second image, an image captured by using the second observation light, the second observation light being light whose center wavelength is shorter than a center wavelength of the first observation light.

12. An endoscope system comprising:
the image processing apparatus according to claim 1;
the display apparatus;
an endoscope that has an insertion section and a handheld operation section, the insertion section to be inserted into a subject and having a tip rigid part, a bending part connected to a base end side of the tip rigid part, and a flexible tube part connected to a base end side of the bending part, the handheld operation section being connected to a base end side of the insertion section;
a light source apparatus that irradiates the subject with the first observation light or the second observation light; and
an imaging unit that has an imaging lens which forms an optical image of the subject and an imaging device on which the optical image is formed by the imaging lens, wherein
the imaging lens is provided at the tip rigid part.

13. The endoscope system according to claim 1, wherein the light source apparatus comprises a white-light laser light source that radiates white-light laser as excitation light; a fluorescent body that emits the white light as the first observation light when irradiated with the white-light laser; and a narrow-band-light laser light source that radiates the narrow-band light as the second observation light.

14. The endoscope system according to claim 1, wherein the light source apparatus comprises a white light source that emits the white light; a white-light filter that allows the white light to pass therethrough; a narrow-band-light filter that allows a component of the narrow-band light in the white light to pass therethrough; and a first filter switching control unit that inserts the white-light filter or the narrow-band-light filter to an optical path of the white light emitted by the white light source.

15. The endoscope system according to claim 12, wherein the light source apparatus irradiates the subject with the first observation light, the first observation light being first narrow-band light that corresponds to any one of a red wavelength range, a blue wavelength range, and a green wavelength range, and irradiates the subject with the second observation light, the second observation light being second narrow-band light that corresponds to any one of the red wavelength range, the blue wavelength range, and the green wavelength range and that has a wavelength range different from a wavelength range of the first narrow-band light.

16. The endoscope system according to claim 15, wherein the light source apparatus comprises a white light source that emits white light including light in the red wavelength range, the blue wavelength range, and the green wavelength range; a first-narrow-band-light filter that allows a component of the first narrow-band light in the white light to pass therethrough; a second-narrow-band-light filter that allows a component of the second narrow-band light in the white light to pass therethrough; and a second filter switching control unit that inserts the first-narrow-band-light filter or the second-narrow-band-light filter to an optical path of the white light emitted by the white light source.

17. An image processing method comprising:
an image acquisition step of acquiring a first image and a second image that are captured at different times, the image acquisition step acquiring the first image that is captured by using a first observation light and the second image that is captured by using a second observation light different from the first observation light;
a mode control step of causing the first image and the second image to be acquired in the image acquisition step in either a first image acquisition mode of acquiring the first image and the second image such that a ratio of the number of acquired frames of the second image to the number of acquired frames of the first image in a predetermined time range is a first ratio, or a second image acquisition mode of acquiring the first image and the second image such that a ratio of the number of acquired frames of the second image to the number of acquired frames of the first image in the time range is a second ratio higher than the first ratio; and a specific target detection step of detecting a specific target from the first image and/or the second image, wherein the mode control step causes the first image and the second image to be acquired in the image acquisition step in the first image acquisition mode or the second image acquisition mode on the basis of a detection result of the specific target, when the specific target detecting unit has detected the region of interest, the mode control unit causes the image acquiring unit to acquire the first image and the second image in the second image acquisition mode until a first termination condition is satisfied, wherein a light source apparatus irradiates a subject with the first observation light, the first observation light being white light including light in a red wavelength range, a blue wavelength range, and a green wavelength range, and irradiates the subject with the second observation light, the second observation light being narrow-band light corresponding to any one of the red wavelength range, the blue wavelength range, and the green wavelength range.

* * * * *